United States Patent
Hassan et al.

(10) Patent No.: US 9,873,859 B2
(45) Date of Patent: *Jan. 23, 2018

(54) MICROORGANISM GROWTH AND PRODUCTS RECOVERY

(71) Applicant: H R D Corporation, Houston, TX (US)

(72) Inventors: Abbas Hassan, Houston, TX (US); Aziz Hassan, Houston, TX (US); Gregory G. Borsinger, Chatham, NJ (US); Rayford Gaines Anthony, College Station, TX (US)

(73) Assignee: H R D Corporation, Houston, TX (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/831,476

(22) Filed: Aug. 20, 2015

(65) Prior Publication Data

US 2017/0051244 A1    Feb. 23, 2017

(51) Int. Cl.
| | |
|---|---|
| C12M 1/00 | (2006.01) |
| C12M 1/42 | (2006.01) |
| C12N 1/06 | (2006.01) |
| C12N 1/12 | (2006.01) |
| C12P 7/64 | (2006.01) |

(52) U.S. Cl.
CPC ............ *C12M 35/04* (2013.01); *C12M 29/06* (2013.01); *C12N 1/066* (2013.01); *C12N 1/12* (2013.01); *C12P 7/6463* (2013.01); *C12M 21/02* (2013.01); *C12M 21/12* (2013.01)

(58) Field of Classification Search
CPC ...... C12M 23/18; C12M 33/00; C12M 35/04; C12M 35/08; C12M 43/02; C12M 47/02; C12M 47/06; C10L 1/026; C10L 2200/0476; C10L 2290/54; C11B 1/04; C11B 1/10; C12P 7/6463; C04B 14/26; C04B 28/02; C04B 14/28; A23V 2002/00; A23V 2250/19; A23V 2250/202; A23V 2300/14; A23V 2300/41; C01F 11/18; C01F 5/24; C01F 11/181; C01F 11/464; C01F 5/40; C01G 11/00; C01G 13/00; C01G 21/14

See application file for complete search history.

(56) References Cited

U.S. PATENT DOCUMENTS

| | | | |
|---|---|---|---|
| 7,762,715 B2 | 7/2010 | Gordon et al. | |
| 8,042,989 B2 | 10/2011 | Gordon et al. | |
| 8,603,198 B2 | 12/2013 | Gordon et al. | |
| 8,673,129 B2 | 3/2014 | Gordon et al. | |
| 8,709,750 B2 | 4/2014 | Gordon et al. | |
| 2010/0233761 A1* | 9/2010 | Czartoski | C12N 1/06 435/71.1 |
| 2014/0093951 A1* | 4/2014 | Hassan | C12M 21/02 435/292.1 |

OTHER PUBLICATIONS

Cabib et al., The Yeast Cell Wall and Septum as Paradigms of Cell Growth and Morphogenesis, The Journal of Biological Chemistry, vol. 276, No. 23, (2001), pp. 19679-19682.

Shirganonkar et al., Comments on the Mechanism of Microbial Cell Disruption in High-Pressure and High-Speed Devices, Mitechnol. Prog. 1998, 14, pp. 657-660.

R.S. Singh, A comparative study on cell disruption methods for release of aspartase from *E. coli* K-12, Indian Journal of Experimental Biology, vol. 51, Nov. 2013, pp. 997-1003.

Allard et al., Occurence of high molecular weight lipds (C80+) in the trilaminar outer cell walls of some freshwater microalgae. A reappraisal of algaenan structure, Organic Geochemistry, 33, 2002, pp. 789-801.

Lee et al., Disruption of microalgal cells for the extraction of lips for biofuels: Processes and specific energy requirements, Biomass and Bioenergy, 46, 2012, pp. 89-101.

Cerri et al., Average shear rate for non-Newtonian fluids in a concentric-tube airlift bioreactor, Biochemical Eng. Journal, 39, 2008, pp. 51-57.

Geciova et al., Methods for disruption of microbial cells for potential use in the dairy industry _ A review, International Dairy Journal, 12, 2002, pp. 541-553.

Gogate et al., A review of applications of cavitation in biochemical engineering/biotechnology, Biochemical Eng. Journal, 44, 2009, pp. 60-72.

Guillaume et al., From compressible to incompressible materials via an asymptotic expansion, Numer. Math. (2002) 91, pp. 649-673.

Peralta-Yahya et al., Identification and microbial production of a terpene-based advanced biofuel, Nature Communications, 2011, pp. 1-8.

Isenschmid et al., The influence of pressure and temperature of compressed CO2 on the survival of yeast cells, Journal of Biotechnology, 39, 1995, pp. 229-237.

Jong et al., Systems biology of yeast: enabling technology for development of cell factories for production of advanced biofuels, ScienceDirect, Current Opinion in Biotechnology, 23, 2012, pp. 624-630.

(Continued)

*Primary Examiner* — Debbie K Ware
(74) *Attorney, Agent, or Firm* — Timothy S. Westby; Peter Hedges LLP

(57) ABSTRACT

Herein disclosed is a method of generating products from microorganisms, comprising super-saturating a liquid medium with a gas consumable by the microorganisms in a high shear device operating at a shear rate of greater than 1,000,000 s−1 to produce a gas-super-saturated (GSS) medium, wherein the GSS medium maintains a GSS level for at least 10 minutes; feeding the GSS medium to microorganisms; allowing the microorganisms to grow by consuming the gas and generate products via photosynthesis or chemosynthesis; and recovering the products. In an embodiment, the microorganisms are genetically modified. In an embodiment, the microorganisms include bacteria, protozoa, algae, or fungi, or a combination thereof. In an embodiment, the gas consumable by the microorganisms is selected from the group consisting of carbon dioxide, nitrogen, air, oxygen, methane, and combinations thereof. A suitable system is also discussed in this disclosure.

15 Claims, 19 Drawing Sheets

(56) References Cited

OTHER PUBLICATIONS

Kleinig et al., On the mechanism of microbial cell disruption in high-pressure homogenisation, Chemical Eng. Science, vol. 53, No. 5, 1998, pp. 891-898.
Krehbiel et al., Algal cell disruption using microbubbles to localize ultrasonic energy, Bioresource Technology, 173, 2015, pp. 448-451.
Markou et al., Cultivation of filamentous cyanobacteria (blue-green algae) in angro-industrial wastes and wastewaters: A review, Applied Energy, 88, (2011), pp. 3389-3401.
Kohles et al., Mechanical Stress Analysis of Microfluidic Environments Designed for Isolated Biological Cell Investigations, Journal of Biochemical Eng., Dec. 2009, 131, pp. 1-10.
Choosing the Best Cell Disruption Method for Research and Pharmaceutical Production, Microfluidics, http://www.mixerequipment.com/f_mic/cell_disruption/cell_disruption.html.
Anton P. J. Middelberg, Process-Scale Disruption of Microorganisms, Biotechnology Advances, vol. 13, No. 3, 1995, pp. 491-551.
Sawant et al., Effect of hydrodynamic cavitation on zooplankton: A tool for disinfection, Biochemical Eng. Journal, 42, 2008, pp. 320-328.
International Search Report and the Written Opinion dated Nov. 4, 2015 for counterpart application PCT/US2015/046342; 11 pages.

\* cited by examiner

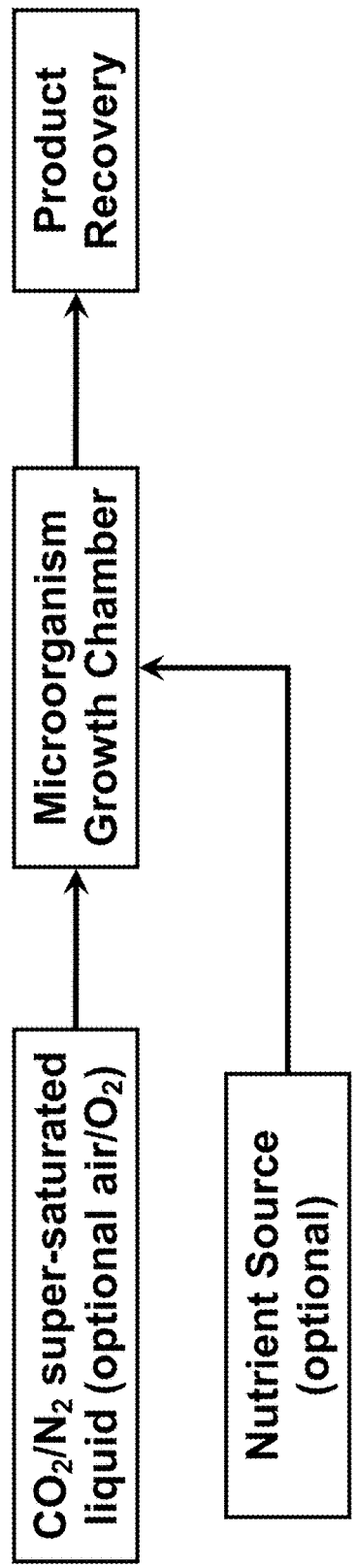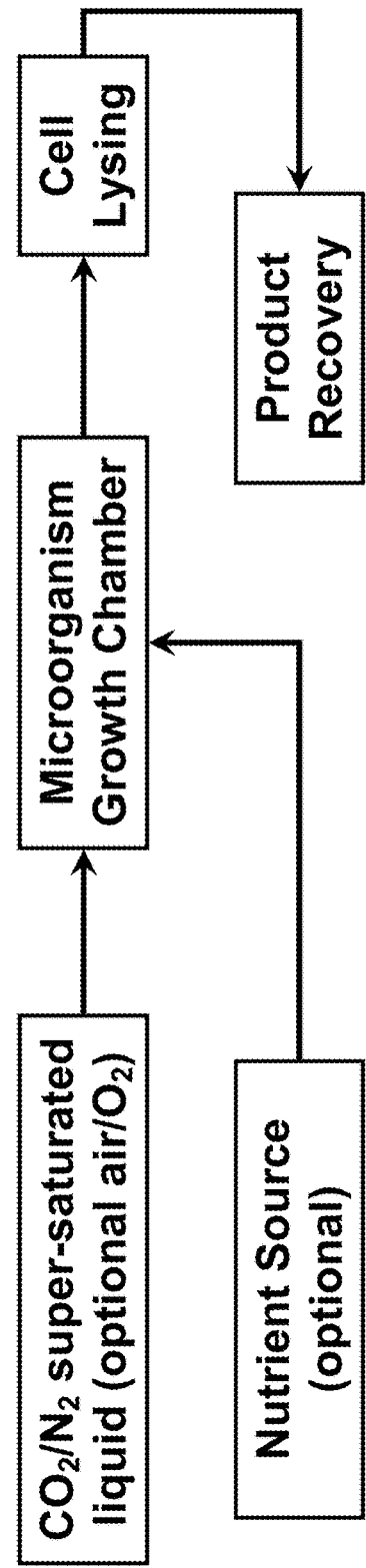
Figure 2
Figure 3

MICROORGANISM GROWTH AND PRODUCTS RECOVERY

STATEMENT REGARDING FEDERALLY SPONSORED RESEARCH or DEVELOPMENT

Not applicable.

BACKGROUND OF THE INVENTION

Technical Field

The present invention relates generally to a process and system of microorganism growth and recovery of valuable products. More particularly, the present invention relates to a system and process for culture of microorganisms and extraction of products using high shear.

Background of the Invention

As is known, ecosystems depend upon the ability of some organisms to convert inorganic compounds into food that other organisms can then exploit. In most cases, primary food production occurs in a process called photosynthesis, which is powered by sunlight. In a few environments, primary production happens though a process called chemosynthesis, which runs on chemical energy. Together, photosynthesis and chemosynthesis fuel all life on Earth. Photosynthesis occurs in plants and some bacteria, wherever there is sufficient sunlight on land, in shallow water, even inside and below clear ice. All photosynthetic organisms use solar energy to turn carbon dioxide and water into sugar and oxygen. There is only one photosynthetic formula: $CO_2 + 6H_2O \rightarrow C_6H_{12}O_6 + 6O_2$.

Chemosynthesis is the use of energy released by inorganic chemical and simple organic compounds such as methane reactions to produce food such as carbohydrates and other organic compounds. Chemosynthesis is at the heart of deep-sea communities, sustaining life in absolute darkness, where sunlight does not penetrate. All chemosynthetic organisms use the energy released by chemical reactions to make a sugar, but different species use different pathways. For example, the most extensive ecosystem based on chemosynthesis lives around undersea hot springs. At these hydrothermal vents, vent bacteria oxidize hydrogen sulfide, add carbon dioxide and oxygen, and produce sugar, sulfur, and water: $CO_2 + 4H_2S + O_2 \rightarrow CH_2O + 4S + 3H_2O$. Other bacteria make organic matter by reducing sulfide or oxidizing methane. Chemosynthetic bacterial communities have been found in hot springs on land and on the seafloor around hydrothermal vents, cold seeps, whale carcasses, and sunken ships.

Recently, there are various concepts of utilizing bacteria (genetically-modified or engineered) to convert carbon (e.g., $CO_2$) to value products (e.g., isobutanol). Clearly, there is a need and interest to continue to develop systems and methods to apply such concepts industrially so that carbon dioxide and other agricultural or municipal wastes can be converted into valuable products.

SUMMARY

Herein disclosed is a method of generating products from microorganisms, comprising super-saturating a liquid medium with a gas consumable by the microorganisms in a high shear device operating at a shear rate of greater than 1,000,000 s−1 to produce a gas-super-saturated (GSS) medium, wherein the GSS medium maintains a GSS level for at least 10 minutes; feeding the GSS medium to microorganisms; allowing the microorganisms to grow by consuming the gas and generate products via photosynthesis or chemosynthesis; and recovering the products.

In an embodiment, the microorganisms are genetically modified. In an embodiment, the microorganisms include bacteria, protozoa, algae, or fungi, or a combination thereof. In an embodiment, the gas consumable by the microorganisms is selected from the group consisting of carbon dioxide, nitrogen, air, oxygen, methane, and combinations thereof.

In an embodiment, the method comprises feeding a nutrient source to the microorganisms in addition to the GSS medium. In an embodiment, the nutrient source comprises municipal waste; sewage waste; paper pulp; chemical and petrochemical; vegetable including grain, sugar; farm discharge; animal farm discharge including beef, pork, poultry; canning discharge, fishing discharge; farming discharge; food processing discharge. In an embodiment, the nutrient source is pretreated to eliminate undesirable pathogens via gas-assisted high shear lysing of pathogen cells or pretreated using high shear to increase the bio-availability of nutrient in the nutrient source. In an embodiment, the products include ethane, ethylene, sugars, acids, lipids, ketones, alcohols, amino acids, proteins, or combinations thereof.

In an embodiment, the products are excreted by the microorganisms extracellularly or wherein the products are generated and kept by the microorganisms intracellularly. In an embodiment, the method comprises lysing cell of the microorganisms to obtain the products when the products are generated and kept by the microorganisms intracellularly. In an embodiment, lysing comprises passing a stream comprising the grown microorganisms through another high shear device; and disintegrating cell walls of and intracellular organelles in the microorganisms to release the products. In an embodiment, disintegration is enhanced by a penetrating gas capable of permeating the cell wall. In an embodiment, enhancement is accomplished by super-saturation of the penetrating gas in the stream or increased gas pressure in a vessel. In an embodiment, the penetrating gas is different from gas produced by the microorganism cell during respiration.

In an embodiment, the method comprises converting at least one of the products to fuel.

Herein also disclosed is a system comprising a tank or pond configured to grow microorganisms; a high shear device configured to process a gas consumable by the microorganisms in a liquid medium operating at a shear rate of greater than 1,000,000 s−1 to form a gas-super-saturated (GSS) liquid stream and feed the GSS stream into the tank or pond for microorganism growth, wherein the GSS stream maintains a GSS level for at least 10 minutes; and a fluid line configured to extract a medium containing microorganisms from the tank or pond.

In an embodiment, the system comprises a nutrient source consumable by the microorganisms, wherein the nutrient source is co-fed to the tank or pond for microorganism growth. In an embodiment, the system comprises a product recovery unit configured to receive the microorganism-containing medium from the fluid line. In an embodiment, the product recovery unit comprises another high shear device configured to disintegrate cell walls of and intracellular organelles in the microorganisms to release products, preferably enhanced by super-saturation of a penetrating gas in the medium or increased gas pressure in a vessel.

In an embodiment, the system of this disclosure is modular and is optionally integrated with an existing facility.

Certain embodiments of the above-described methods or systems potentially provide overall cost reduction by providing increased inhibition per unit of inhibitor consumed, permitting increased fluid throughput, permitting operation at lower temperature and/or pressure, and/or reducing capital and/or operating costs. These and other embodiments and potential advantages will be apparent in the following detailed description and drawings.

BRIEF DESCRIPTION OF THE DRAWINGS

For a more detailed description of the preferred embodiment of the present invention, reference will now be made to the accompanying drawings, wherein:

FIG. 2 illustrates an overall process flow diagram for microorganism culture and product recovery, according to an embodiment of this disclosure.

FIG. 3 illustrates another overall process flow diagram for microorganism culture and product recovery, according to an embodiment of this disclosure.

FIG. 8b is a detailed drawing of the CO2 diffuser positioned within the influent stream to the high shear unit as illustrated in FIG. 8a.

DETAILED DESCRIPTION

Figure 1:
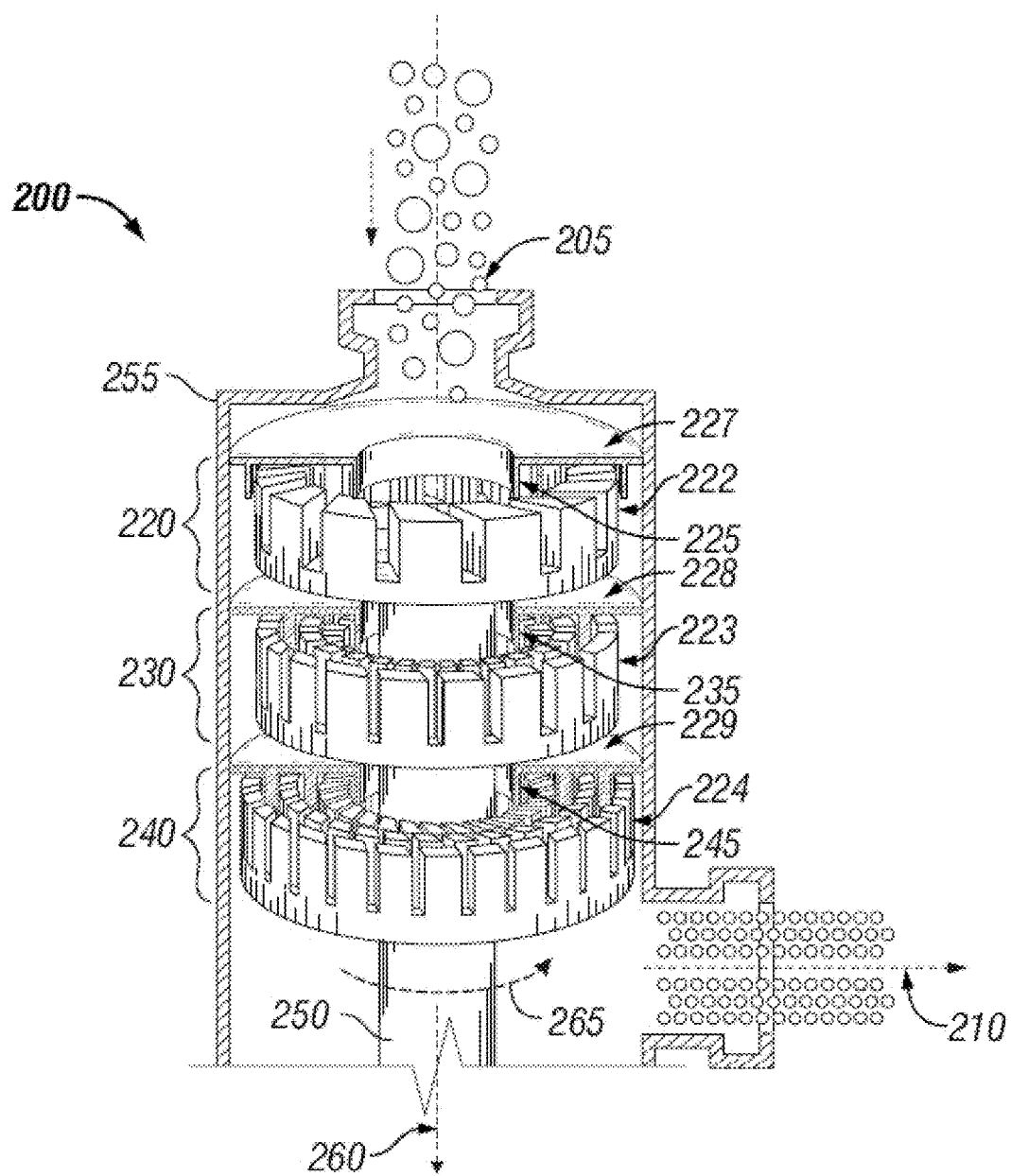
FIG. 1 is a longitudinal cross-section view of a multistage high shear device, as employed in an embodiment of the system.

This disclosure relates to microorganism culture and product recovery. Such microorganisms include bacteria, protozoa, algae, or fungi. The following discussion related to bacteria applies to any suitable microorganisms.

Various strains of bacteria and/or combinations thereof, particularly those that are genetically-modified or engineered, are able to convert carbon into various valuable products, e.g., ethane, ethylene, sugars, acids, lipids, ketones, and alcohols. For example, cyanobacteria and microalgae that consume CO2 have been identified and can produce hydrogen, ethanol sugars and carbohydrates. Recently engineered CO2 consuming bacteria have been able to produce isobutyraldehyde. Such products may then be further processed into desired products, e.g., fuel.

A key component to the success of this technology is the amount of $CO_2$ deliverable to the microorganism during culture. It has been unexpectedly found that the method and system of this application is able to super saturate a liquid medium with $CO_2$ and produce stable $CO_2$-super-saturated (CO2SS) streams for the use of microorganism culture. As such, the process and system of this application is able to reduce or eliminate the bottleneck of insufficient consumable $CO_2$ during microorganism culture and thus for deriving valuable products. The method and system of this application are capable to reducing this hindrance and significantly improve efficiency for microorganism culture and product recovery.

Another aspect of the present invention is in the control and utilization of nitrates in wastewater. The control of nitrates in wastewater can be controlled by algae through the following process:

For ammonia as the nitrogen source,

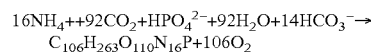

or, for nitrate as the nitrogen source,

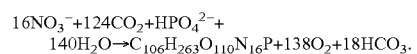

Both reactions are endothermic, i.e., requires energy input, which for algae would be supplied by solar energy. Nitrates in wastewater can also be controlled by means of bacteria such as *Nitrosomonas* and *Nitrobacter* that process nitrogen containing waste through chemosynthetic autotrophic mechanisms. Chemosynthetic autotrophic bacteria derive their energy from inorganic compounds as opposed to heterotrophic bacteria that derive energy from organic compounds. These bacteria function by nitrification of ammonia-nitrogen to nitrite-nitrogen and finally to nitrate-nitrogen. Nitrification is a two-step process, where ammonia is first oxidized to nitrite and then nitrite is oxidized to nitrate. This process requires pond aeration that can be enhanced through high shear processing of air and/or oxygen. A representative example of this process is as follows:

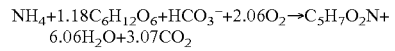

Given the control of nitrates, value added products such as shrimp can be grown in such ponds and used as a source of protein consumption.

In a further embodiment, nitrogen gas and optionally oxygen or air is processed in a high shear device together with a liquid growth medium where bacteria and other prokaryotes are being cultured in the presence of nutrients derived from waste sources to produce value added products through the process of fixation of nitrogen. Super saturation can be for the entire or a portion of the stream. The method and system of this disclosure is able to introduce nitrogen gas into an environment where nitrogen fixing bacteria are present with the benefit of enhanced nitrogen fixing bacterial growth. In some cases, air may be conveniently used as the source of nitrogen gas.

Fixation of Nitrogen for cell growth involves the following process:

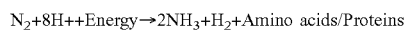

$$N_2+8H++Energy \rightarrow 2NH_3+H_2+Amino\ acids/Proteins$$

Yet another aspect of the present invention is the use of high shear in enhancing the production of bacteria producing linear alkanes that can be used as a replacement for petroleum products. Genetic modification of bacteria has resulted in bacteria that can produce low molecular weight hydrocarbons that can be utilized in chemical and petrochemical applications. Bacteria such as cyanobacterium can be used to consume additional $CO_2$ produced in the process or supplied from an external source.

Another aspect of the present invention is to utilize supersaturation to enhance the growth of methane consuming bacteria. Methane has been identified as a significant contributor to global warming. The oxygen-producing bacterium, provisionally named Methylomirabilis oxyfera, grows in a layer of methane-rich but oxygen-poor mud at the bottom of rivers and lakes. The microbes live on a diet of methane and nitrogen oxides, such as nitrite and nitrate. These nitrogen-containing compounds are especially abundant in sediment contaminated by agricultural runoff. Methanotrophs (sometimes called methanophiles) are prokaryotes that are able to metabolize methane as their only source of carbon and energy. They can grow aerobically or anaerobically and require single-carbon compounds to survive.

As such, the method and system of this disclosure applies to any suitable gas consumable by microorganism to produce desired products. Such gases include carbon dioxide, nitrogen, air, oxygen, methane, or any combinations thereof etc. The discussion below is more focused on carbon dioxide and nitrogen. It is herein made clear that all such suitable gases are within the scope of this disclosure.

The instant method and system utilize a rotor-stator high shear device to super saturate a liquid medium with $CO_2$. Such CO2SS liquid medium maintains a $CO_2$-super-saturated (CO2SS) level for more than 10 minutes. In some cases, such CO2SS liquid medium maintains a CO2SS level for more than 1 hour. In some cases, such CO2SS liquid medium maintains a CO2SS level for more than 10 hours. In some cases, such CO2SS liquid medium maintains a CO2SS level for more than 1 day. In some cases, such CO2SS liquid medium maintains a CO2SS level for more than 2 days. In some cases, such CO2SS liquid medium maintains a CO2SS level for more than 3 days. In some cases, such CO2SS liquid medium maintains a CO2SS level for more than 4 days. The meaning of CO2SS level is that the high shear processed liquid medium has a $CO_2$ content that is higher than the equilibrium $CO_2$ content with no high shear processing.

The instant method and system utilize a rotor-stator high shear device to super saturate a liquid medium with $N_2$. Such N2SS liquid medium maintains a $N_2$-super-saturated (N2SS) level for more than 10 minutes. In some cases, such N2SS liquid medium maintains a N2SS level for more than 1 hour. In some cases, such N2SS liquid medium maintains a N2SS level for more than 10 hours. In some cases, such N2SS liquid medium maintains a N2SS level for more than 1 day. In some cases, such N2SS liquid medium maintains a N2SS level for more than 2 days. In some cases, such N2SS liquid medium maintains a N2SS level for more than 3 days. In some cases, such N2SS liquid medium maintains a N2SS level for more than 4 days. The meaning of N2SS level is that the high shear processed liquid medium has a N2 content that is higher than the equilibrium N2 content with no high shear processing. Examples of rotor-stator high shear device include mechanical pulpers, refiners (e.g., Beloit Jones DD 3000 refiners, Voith Twin Flo TFE Refiner, Metso JC series refiners), mills. Papermaking refiners can be either disc refiners or conical refiners, pulp enters through a feed port, travels between a conical rotor and stator and then leaves through the discharge port. The rotor and stator will have a bar and groove pattern. Only one of the elements will rotate (the rotor). The gap between the refiners can be controlled by pushing the rotor and stator together. A disc refiner is very similar to the conical refiner. The pulp travels between two discs with bars and grooves. There are essentially three categories of disc refiner:

1. Single disc refiners, where the pulp goes between a rotating rotor and a stationary stator.
2. Twin refiner where the rotor and stator both rotate.

In papermaking the refiner serves to increase the flexibility of the cell wall in order to promote increased contact area, and also to fibrillate the external surface of the cell wall to further promote the formation of hydrogen bonds as well as increase the total surface area of fiber available for bonding.

The present invention can utilize any of the rotor stator designs and configurations to create high shear for the purpose of enhancing cell growth through gas super saturation and lysing cells.

Furthermore, it has been unexpectedly discovered that lysis of cells is enhanced by using a high shear device coupled with introduction of a gas capable of permeating the cell wall and thus expanding the cell and reducing the cell wall integrity. Such enhancement is achieved by high shear coupled with gas super-saturation in the culture medium during lysing or high shear coupled with a gas-pressurized vessel. The high shear device may be of a rotor-stator design. Migration of gas is enhanced through super saturation of gases by means of high shear or via increased pressures such as in a vessel under elevated pressure. Various techniques that utilize pressure to enhance cell lysing are known to those experienced in the art including what is commonly referred to as a French Press.

In an embodiment, enhancing cell lysing involves selection of a suitable gas that preferentially penetrates cell walls. The selection of a suitable gas is dependent on the nature of the cell and the gas produced by the cell during respiration. As an example, yeast that produce carbon dioxide did not exhibit enhanced lysing when exposed to supersaturated carbon dioxide while yeast exposed to supersaturated oxygen did exhibit enhanced lysing. The enhancement of yeast lysing while exposed to supersaturated oxygen was attributed to the differential gas pressure across the cell wall and the observed expansion of the cell under exposure to oxygen as opposed to carbon dioxide.

The disclosed method and system of enhanced cell lysing is be applied to any gas producing algae, bacteria, yeast, or fungus. Selection of a suitable supersaturated gas is dependent on the nature of the gas being produced by the cell during respiration. Thus, a cell such as algae producing oxygen and would be expected to have a higher concentration of oxygen within the cell wall would not be expected to experience enhanced lysing from exposure to supersaturated oxygen. Gases such as carbon dioxide, nitrogen, sulfur oxides, and other gases that would expect to migrate from the medium to within the cell walls and reduce cell wall integrity would be expected to enhance lysing. Similarly it has been shown that yeast producing carbon dioxide did not experience enhanced lysing when exposed to supersaturated carbon dioxide but did exhibit enhanced lysing when exposed to supersaturated oxygen.

Although oxygen, nitrogen carbon dioxide and sulfur oxide have been noted as gases to be used in enhancing cell lysing, other suitable gases can be used to obtain the same effect of reducing cell wall integrity, e.g., hydrogen. In an embodiment, hydrogen is super saturated into a medium and contributes to enhanced lysing in cells that are not producing hydrogen during respiration.

High Shear Device.

The high shear device of this application is shown in FIG. 1 and described herein. Although only one high shear device is shown in FIG. 1, it should be understood that some embodiments of the system may have two or more high shear devices arranged either in series or parallel flow. HSD 200 is a mechanical device that utilizes one or more generator comprising a rotor/stator combination, each of which has a gap between the stator and rotor. The gap between the rotor and the stator in each generator set may be fixed or may be adjustable. HSD 200 is configured in such a way that it is capable of producing submicron and micron-sized bubbles or droplets of inhibitor in a continuous phase comprising the carrier flowing through the high shear device. The high shear device comprises an enclosure or housing so that the pressure and temperature of the fluid therein may be controlled.

High shear devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range. The high shear device also includes attrition mills.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.025 mm to 10 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). A colloid mill, for example, may have a tip speed in excess of 22.9 m/s (4500 ft/min) and may exceed 40 m/s (7900 ft/min). For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the stream of products to be reacted. For example, in HSD 200, a tip speed in excess of 22.9 m/s (4500 ft/min) is achievable, and may exceed 40 m/s (7900 ft/min). In some embodiments, HSD 200 is capable of delivering at least 300 L/h at a tip speed of at least 22.9 m/s (4500 ft/min). The power consumption may be about 1.5 kW. HSD 200 combines high tip speed with a very small shear gap to produce significant shear on the material being processed. The amount of shear will be dependent on the viscosity of the fluid in HSD 200. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases, these local pressure and temperature elevations may persist for nano or pico seconds.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure of HSD 200 is greater than 1000 watts per cubic meter of fluid therein. In embodiments, the energy expenditure of HSD 200 is in the range of from about 3000 W/m$^3$ to about 7500 W/m$^3$.

The shear rate is the tip speed divided by the shear gap width (minimal clearance between the rotor and stator). The shear rate generated in HSD 200 may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In some embodiments the shear rate is at least 2,000,000 s$^{-1}$. At high shear rates (e.g., above 1,000,000 s$^{-1}$ or 1,600,000 s$^{-1}$ or 2,000,000 s$^{-1}$), the HSD is able to super-saturate the liquid/medium with a gas (or gases), which is advantageous for bacterial culture wherein it is necessary and desirable to deliver high concentrations of $CO_2$ to bacteria.

The shear rate is the tip speed divided by the shear gap width (minimal clearance between the rotor and stator). In some embodiments the shear rate is at least 1,600,000 s$^{-1}$. In some embodiments the shear rate is at least 3,000,000 s$^{-1}$. In some embodiments the shear rate is at least 5,000,000 s$^{-1}$. In some embodiments the shear rate is at least 7,000,000 s$^{-1}$. In some embodiments the shear rate is at least 9,000,000 s$^{-1}$. In embodiments where the rotor has a larger diameter, the shear rate may exceed about 9,000,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

HSD 200 is capable of highly dispersing the inhibitor into a continuous phase comprising the carrier, with which it would normally be immiscible. In some embodiments, HSD 200 comprises a colloid mill. Suitable colloidal mills are manufactured by IKA® Works, Inc. (Wilmington, N.C.), for example. In some instances, HSD 200 comprises the Dispax Reactor® of IKA® Works, Inc.

The high shear device comprises at least one revolving element that creates the mechanical force applied to the fluid therein. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.025 mm (0.001 inch) to about 3 mm (0.125 inch). In certain embodiments, the minimum clearance (shear gap width) between the stator and rotor is about 1.5 mm (0.06 inch). In certain configurations, the minimum clearance (shear gap) between the rotor and stator is at least 1.7 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, HSD comprises a single stage dispersing chamber (i.e., a single rotor/stator combination, a single generator). In some embodiments, high shear device 200 is a multiple stage inline disperser and comprises a plurality of generators. In certain embodiments, HSD 200 comprises at least two generators. In other embodiments, high shear device 200 comprises at least 3 high shear generators. In some embodiments, high shear device 200 is a multistage mixer whereby the shear rate (which, as mentioned above, varies proportionately with tip speed and inversely with rotor/stator gap width) varies with longitudinal position along the flow pathway, as further described herein below.

In some embodiments, each stage of the external high shear device has interchangeable mixing tools, offering flexibility. For example, the DR 2000/4 Dispax Reactor® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble or droplet size (e.g., gas bubbles or liquid droplets of inhibitor). In some embodiments, each of the stages is operated with super-fine generator. In some embodiments, at least one of the generator sets has a rotor/stator minimum clearance (shear gap width) of greater than about 5 mm (0.2 inch). In alternative embodiments, at least one of the generator sets has a minimum rotor/stator clearance of greater than about 1.7 mm (0.07 inch).

Referring now to FIG. 1, there is presented a longitudinal cross-section of a suitable high shear device 200. High shear device 200 of FIG. 1 is a dispersing device comprising three stages or rotor-stator combinations. High shear device 200 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 may be fixably coupled to the wall 255 of high shear device 200.

As mentioned hereinabove, each generator has a shear gap width which is the minimum distance between the rotor and the stator. In the embodiment of FIG. 1, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm. In certain embodiments, each of three stages is operated with a super-fine generator, comprising a shear gap of between about 0.025 mm and about 4 mm.

High shear device 200 is configured for receiving at inlet 205 a fluid mixture from line 13. The mixture comprises inhibitor as the dispersible phase and carrier fluid as the continuous phase. Feed stream entering inlet 205 is pumped serially through generators 220, 230, and then 240, such that product dispersion is formed. Product dispersion exits high shear device 200 via outlet 210 (and line 18 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create product dispersion. Product dispersion exits high shear device 200 via high shear outlet 210.

The product dispersion has an average droplet or gas bubble size less than about 5 lam. In embodiments, HSD 200 produces a dispersion having a mean droplet or bubble size of less than about 1.5 μm. In embodiments, HSD 200 produces a dispersion having a mean droplet or bubble size of less than 1 μm; preferably the droplets or bubbles are sub-micron in diameter. In certain instances, the average droplet or bubble size is from about 0.1 μm to about 1.0 μm. In embodiments, HSD 200 produces a dispersion having a mean droplet or bubble size of less than 400 nm. In embodiments, HSD 200 produces a dispersion having a mean droplet or bubble size of less than 100 nm. The dispersion may be capable of remaining dispersed at atmospheric pressure for at least about 15 minutes.

Without wishing to be limited to a particular theory, it is believed that the level or degree of high shear may be sufficient to increase rates of mass transfer and also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon,"

Microorganism Culture to Generate Products.

In an embodiment, a method of this disclosure to recover products from microorganisms comprises super-saturating a liquid medium with carbon dioxide or nitrogen in a high shear device operating at a shear rate of greater than 1,000,000 s$^{-1}$ to produce a $CO_2$ or $N_2$ super-saturated (CO2SS or N2SS) medium, wherein said CO2SS or N2SS medium maintains a CO2SS or N2SS level for at least 10 minutes; feeding said CO2SS or N2SS medium to microorganisms; allowing the microorganisms to grow by consuming carbon dioxide or nitrogen and generate products via photosynthesis or chemosynthesis; and recovering said products. Carbon dioxide may be obtained from any source, such as power plants, refineries, paper mills, gas to liquids (GTL) plants. In various embodiments, the microorganisms are genetically modified or engineered. In some cases, the high shear device operates at a shear rate of greater than 2,000,000 s$^{-1}$. In some cases, the CO2SS or N2SS medium maintains a CO2SS or N2SS level for at least 1 hour.

In various embodiments, a nutrient source is also fed to the microorganisms in addition to the CO2SS or N2SS medium. Such nutrient source is any suitable agricultural or industrial discharge or waste as known to one skilled in the art, such as, municipal waste, sewage waste, paper pulp, chemical and petrochemical, vegetable (grain, sugar), farm discharge, animal farm discharge (beef, pork, poultry), canning discharge, or fishing discharge as well as other nutrient containing discharge from other farming and farm product processing operations.

In various embodiments, the nutrient source may contain undesirable microorganisms, e.g., sewage waste. These undesirable microorganisms are herein called pathogens in this disclosure. As such, the nutrient is pretreated before fed to the microorganisms. The pretreatment comprises lysing the cells of the undesirable pathogens using a high shear device assisted by a penetrating gas (e.g., in super-saturation state) as discussed herein. Preferably, the penetrating gas is different from the gas produced by the cells of the pathogens during respiration. For example, the nutrient source is super saturated with a blend of oxygen (air or oxygen-enriched air or oxygen) and carbon dioxide using a high shear device and then passed through another high shear device. Or the nutrient source is pretreated in a high shear device while a suitable penetrating gas or gas combination is simultaneously fed into the high shear device. Alternatively, the nutrient source is held under pressure in a French Press containing a pressurized penetrating gas for a period of time and then processed in a high shear device. By such pretreatment, the pathogens are eliminated and the nutrient source is suitable for microorganism culture. Alternate treatments to eliminate unwanted pathogens are known to those experienced in the art.

In other embodiments, the pretreatment of the nutrient source using high shear (with or without gas assistance) is able to break down the nutrient (e.g., sugar, carbohydrate) in the nutrient source to miniscule size so that it is easily digested/consumed by the microorganisms. As such, the bio-availability of the dispersed nutrient is significantly increased to promote microorganism growth.

In various embodiments, the microorganisms-generated products include ethane, ethylene, sugars, acids, lipids, ketones, alcohols, amino acids, proteins, or combinations thereof. The genetic modification of said microorganisms depends on the desired products and/or the type of the nutrient source to be consumed. In some cases, the products are excreted by said microorganisms extracellularly. In some cases, the products are generated and kept by said microorganisms intracellularly. In such cases, the microorganism cells are lysed before product recovery. In an embodiment, lysing the microorganism cells comprises passing a stream comprising the grown microorganisms through another high shear device; and disintegrating cell walls of and intracellular organelles in the microorganisms to release the products. In some cases, the high shear device for cell lysing is operated at a shear rate of 20,000 to 10,000,000, or alternatively 100,000 to 2,000,000, or alternatively 200,000 to 500,000 (in inverse seconds, $s^{-1}$). In some cases, the high shear device for cell lysing is operated at a shear rate of 200,000 $s^{-1}$ or above. In some cases, the high shear device for cell lysing is operated at a shear rate of 200,000 $s^{-1}$ or above. In some cases, the high shear device for cell lysing is operated at a shear rate of 300,000 $s^{-1}$ or above. In some cases, the high shear device for cell lysing is operated at a shear rate of 400,000 $s^{-1}$ or above. In some cases, the high shear device for cell lysing is operated at a shear rate of 500,000 $s^{-1}$ or above. In some cases, the high shear device for cell lysing is operated at a shear rate of 600,000 $s^{-1}$ or above. In some cases, the high shear device for cell lysing is operated at a shear rate of 700,000 $s^{-1}$ or above. In some cases, the high shear device for cell lysing is operated at a shear rate of 800,000 $s^{-1}$ or above. In some cases, the high shear device for cell lysing is operated at a shear rate of 900,000 $s^{-1}$ or above. In some cases, the high shear device for cell lysing is operated at a shear rate of 1,000,000 $s^{-1}$ or above. In some cases, the high shear device for cell lysing is operated at a shear rate of 2,000,000 $s^{-1}$ or above. It should be noted that as the shear rate is calculated by measuring the shear gap and rotor speed, in the case where the configuration of the rotor stator is a disc or conical the shear rate (inverse seconds) will vary across the disc or cone as the apparent rotational speed will vary across the radius of the disc. In such cases, the ranges mentioned above apply to the average shear rates of such rotor-stator devices.

In an embodiment, 30% or more of the product is released for recovery. In an embodiment, 30% or more of the product is released for recovery. In an embodiment, 40% or more of the product is released for recovery. In an embodiment, 50% or more of the product is released for recovery. In an embodiment, 60% or more of the product is released for recovery. In an embodiment, 70% or more of the product is released for recovery. In an embodiment, 80% or more of the product is released for recovery. In an embodiment, 90% or more of the product is released for recovery.

In an embodiment, recovering said products comprises separating said byproducts from the medium. Such separation comprises a process selected from the group consisting of washing, sedimentation, centrifugation, filtration, vaporization, distillation, freezing, extraction, or combinations thereof. Any suitable separation process/method as known in the art is considered to be within the scope of this disclosure. In a further embodiment, at least one of said products is converted to fuel by any mean known in the art.

In an embodiment, 30% or more of product is released and recovered. In an embodiment, 40% or more of product is released and recovered. In an embodiment, 40% or more of product is released and recovered. In an embodiment, 50% or more of product is released and recovered. In an embodiment, 60% or more of product is released and recovered. In an embodiment, 70% or more of product is released and recovered. In an embodiment, 80% or more of product is released and recovered. In an embodiment, 90% or more of product is released and recovered.

System.

In an embodiment, a system of recover products from microorganisms comprises a tank or pond configured to grow microorganisms; a high shear device configured to process carbon dioxide or nitrogen in a liquid medium operating at a shear rate of greater than 1,000,000 $s^{-1}$ to form a carbon dioxide super-saturated (CO2SS or N2SS) liquid stream and feed said CO2SS or N2SS stream into the tank or pond for microorganism growth, wherein said CO2SS or N2SS stream maintains a CO2SS or N2SS level for at least 10 minutes; and a fluid line configured to extract a medium containing microorganisms from the tank or pond. In an embodiment, the system comprises a nutrient source consumable by said microorganisms, wherein said nutrient source is co-fed to the tank or pond for microorganism growth. In another embodiment, the system comprises a product recovery unit configured to receive said microorganism-containing medium from the fluid line.

In some cases, the product recovery unit comprises another high shear device configured to disintegrate cell walls of and intracellular organelles in the microorganisms to release products. In various embodiments, the system of this disclosure is modular, versatile, and movable. As such, it is easy to integrate such systems with an existing facility for carbon dioxide sequestration, waste management, and bio-fuel production. As is clear to one skilled in the art, such integration has numerous benefits and fulfills a multitude of purposes. In some case, this system is integrated with an existing facility, e.g., a power plant, a food processing unit, sewage treatment plant, a paper mill, a refinery.

In an embodiment, as illustrated schematically in FIG. 2, an overall process flow of microorganism culture and product recovery is shown. A liquid super saturated with $CO_2$ or $N_2$ (and optionally $O_2$/air) by the use of a high shear device is introduced into a microorganism growth chamber. In some cases, a nutrient source is also fed to the microorganisms in addition to the CO2SS or N2SS liquid. Oxygen or air is added in some cases, e.g., the use of sewage waste as the nutrient source so that the BOD and COD contents would meet standards. The microorganisms consume the $CO_2$ or $N_2$ and the nutrient and generate products via photosynthesis or chemosynthesis. After the desired growth of microorganisms is achieved, a medium containing microorganisms is sent to the product recovery unit. In this case, the products are excreted by the microorganisms extracellularly and the remains (containing microorganisms) from the separated products may be recycled to generate more products.

In an embodiment, as shown in FIG. 3, another overall process flow of microorganism culture and product recovery is shown. A liquid super saturated with $CO_2$ or $N_2$ (and optionally $O_2$/air) by the use of a high shear device is introduced into a microorganism growth chamber. In some cases, a nutrient source is also fed to the microorganisms in addition to the CO2SS or N2SS liquid. Oxygen or air is added in some cases, e.g., the use of sewage waste as the nutrient source so that the BOD and COD contents would meet standards. The microorganisms consume the $CO_2$ or $N_2$ and the nutrient and generate products via photosynthesis or chemosynthesis. After the desired growth of microorganisms is achieved, the microorganism cells are lysed and the products are released and subsequently recovered. In this case, the products are generated and kept by said microorganisms intracellularly. The remains from the separated products may be used to produce animal feeds, fertilizers, etc.

Features.

The disclosed method and system are versatile, low in capital cost and operational cost. Furthermore, the system is modular, making it easy to be integrated into any existing facility or infrastructure, e.g., power plants, sewage treatment plants, canning factories, food processing units, etc.

The separated solids may be recycled and used for many other purposes, such as producing pharmaceuticals, fertilizers, animal feeds, etc.

Example 1

Effects of Super-Saturation Using High Shear

Carbon dioxide ($CO_2$) is readily soluble in water in the form of a dissolved gas. Surface waters normally contain less than 10 ppm free carbon dioxide, while some ground waters may easily exceed that concentration. Over the typical temperature range (0-30° C.), the solubility is about 200 times that of oxygen. When CO2 reacts with water, it immediately forms carbonic acid ($H_2CO_3$), which is relatively unstable. This further dissociates to form bicarbonate ($HCO_3$) and carbonate ($CO_3^{2-}$) ions.

Compared with oxygen, the estimation of carbon dioxide in water presents much greater difficulties. Although pH is widely used to measure the presence of carbonic acids and carbonates in solution, the presence of carbonate forming ions, including calcium, magnesium, and sodium may interfere with total dissolved carbon measurements.

The total inorganic carbon (TIC) or dissolved inorganic carbon (DIC) is the sum of inorganic carbon species (including carbon dioxide, carbonic acid, bicarbonate anion, and carbonate) in a solution. It is customary to express carbon dioxide and carbonic acid simultaneously as CO2*. TIC is a key parameter when making measurements related to the pH of natural aqueous systems, and carbon dioxide flux estimates:

$$TIC=[CO_2^*]+[HCO_3^-]+[CO_3^{2-}]$$

where, TIC is the total inorganic carbon; $[CO_2^*]$ is the sum of carbon dioxide and carbonic acid concentrations ($[CO_2^*]=[CO_2]+[H_2CO_3]$); $[HCO_3^-]$ is the bicarbonate concentration; $[CO_3^{2-}]$ is the carbonate concentration.

Each of these species are related by the following pH-driven chemical equilibrium equation:

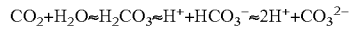

$$CO_2+H_2O \rightleftharpoons H_2CO_3 \rightleftharpoons H^+ + HCO_3^- \rightleftharpoons 2H^+ + CO_3^{2-}$$

The concentrations of the different species of DIC (and which species is dominant) depend on the pH of the solution, as shown by a Bjerrum plot. Total inorganic carbon is typically measured by the acidification of the sample which drives the equilibria to $CO_2$. This gas is then sparged from solution and trapped, and the quantity trapped is then measured, usually by infrared spectroscopy using a Total Organic Carbon (TOC) analyzer.

Total Organic Carbon (TOC) is a sum measure of the concentration of all organic carbon atoms covalently bonded in the organic molecules of a given sample of water. TOC is typically measured in Parts Per Million (ppm or mg/L). As a sum measurement, Total Organic Carbon does not identify specific organic contaminants. It will, however, detect the presence of all carbon-bearing molecules, thus identifying the presence of any organic contaminants, regardless of molecular make-up.

A typical analysis for TOC measures both the Total Carbon (TC) as well as Inorganic Carbon (IC, or carbonate). Subtracting the Inorganic Carbon from the Total Carbon yields TOC. (TC−IC=TOC).

Dissolved oxygen can easily be measured and reported as mg/L using a dissolved oxygen probe (Milwaukee Instruments) submerged in solution.

Figure 4:
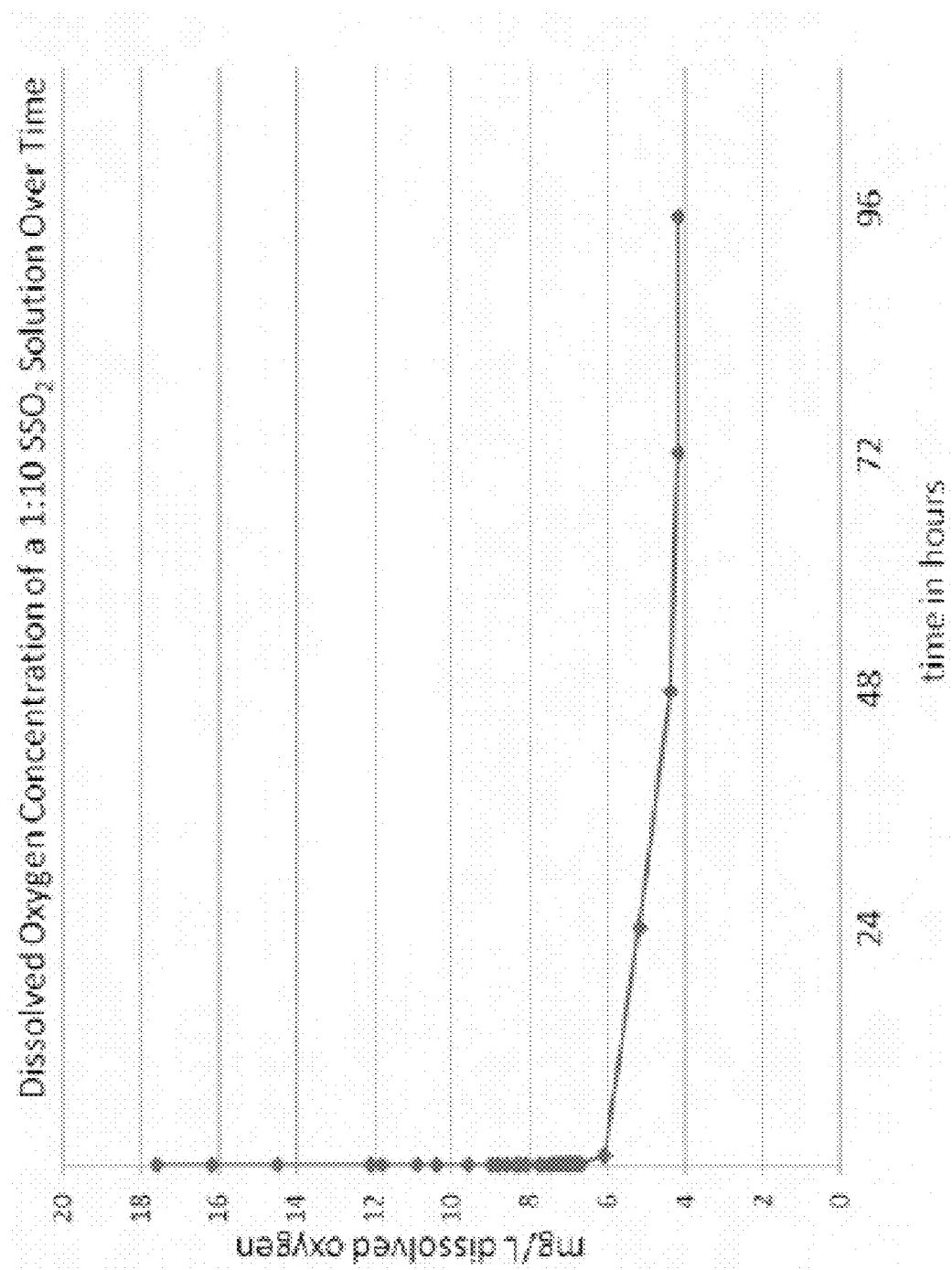
FIGS. 4 and 5 show dissolved oxygen concentration of a 1:10 supersaturated oxygen solution in Example 1.
Figure 5:
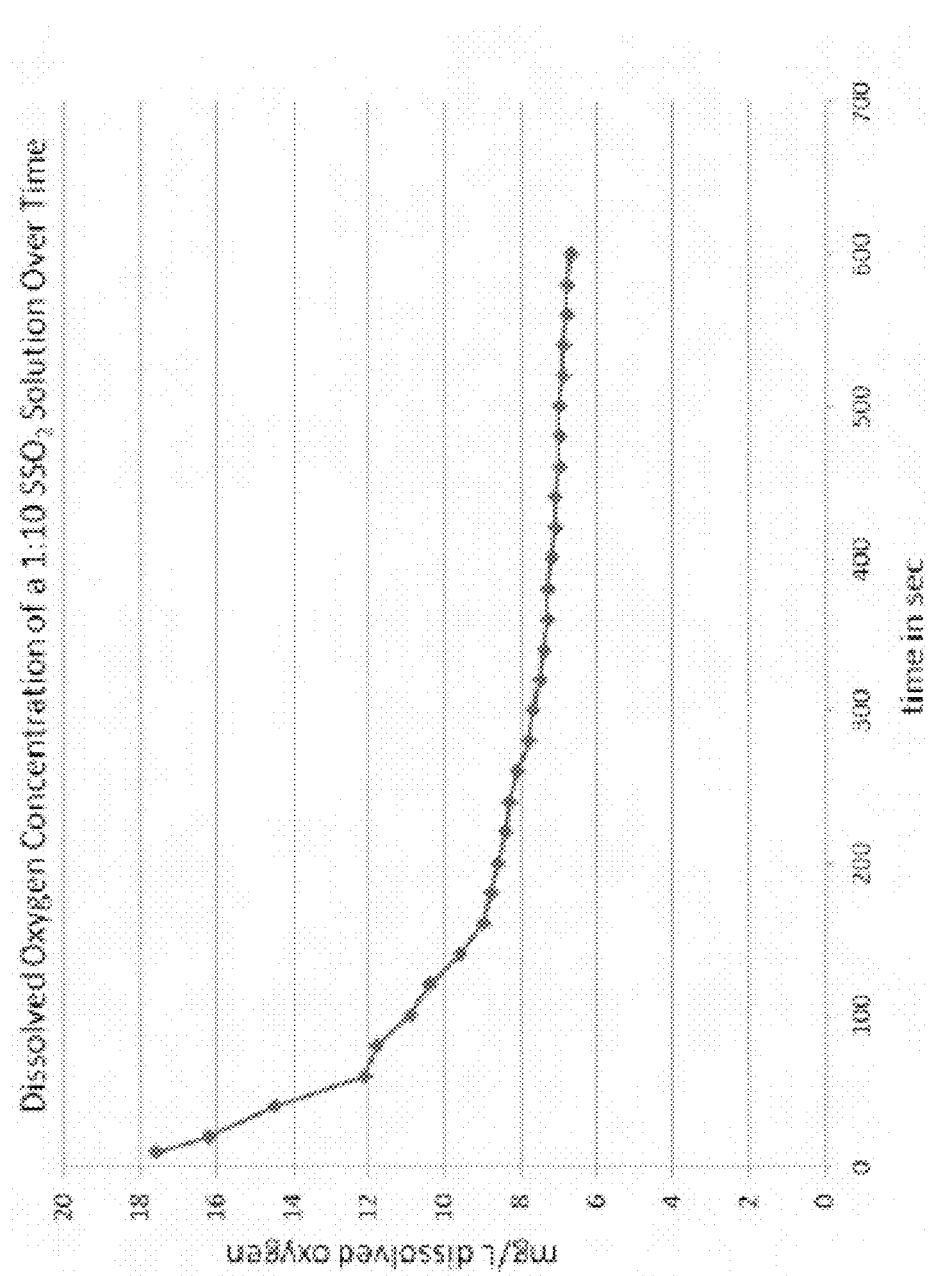

Initially, 3 L of distilled water were sheared using a high shear device to monitor the concentration of dissolved oxygen in solution over time. However, the concentration of dissolved oxygen exceeded the measurement capability of the dissolved oxygen probe (MW600, Milwaukee Instruments). Therefore, the test was repeated and the supersaturated oxygen solution was immediately diluted 1:10 prior to measurements. In this case, three liters of distilled water were sheared in the presence of oxygen gas and quickly diluted to a 1:10 concentration in 3 one liter flasks. The concentration of the 1:10 supersaturated oxygen solution was initially measured to be an average of 17.6 mg/L. Within 5 minutes, the concentration of the dissolved oxygen dropped to an average of 6.7 mg/L, a 62% loss of dissolved oxygen in the 1:10 solution (FIGS. 4 and 5). To establish the dissolved oxygen equilibrium point, the dissolved oxygen concentration was monitored daily for a total of 4 days. The data show that a dissolved oxygen equilibrium point was reached between 2 and 3 days following supersaturation, and that the dissolved oxygen concentration maintained a final concentration of 4.3 mg/L. As a control, the dissolved oxygen concentration of distilled water was concurrently monitored at 4.3 mg/L throughout the test. These results indicate that the tested shear technology effectively supersaturates distilled water with oxygen; however, this effect is of very short duration.

Similar to the supersaturated oxygen tests, 3 liters of distilled water were sheared in the presence of carbon dioxide and evaluated for total dissolved carbon using a TOC analyzer. Also like the dissolved oxygen tests, the concentration of dissolved carbon in the neat solution exceeded the instrument's measurement capability. Therefore, the neat solution was diluted to 1:10, 1:100, and 1:1000 in triplicate to quantify dissolved carbon over time. Potassium hydrogen phthalate (KHP) is commonly used as a standard for dissolved carbon measurements by TOC. A freshly prepared 10 g/L KHP solution of was diluted into a concentration range between 1 mg/L-1000 mg/L and used to establish the dissolved carbon standard curve. This range of standards was prepared daily, while the original diluted supersaturated CO2 solutions were maintained in septum-sealed glass vials and measured daily to quantify dissolved carbon over time and establish the SSCO2 equilibrium point. The pH of each solution was concurrently monitored.

Figure 6:
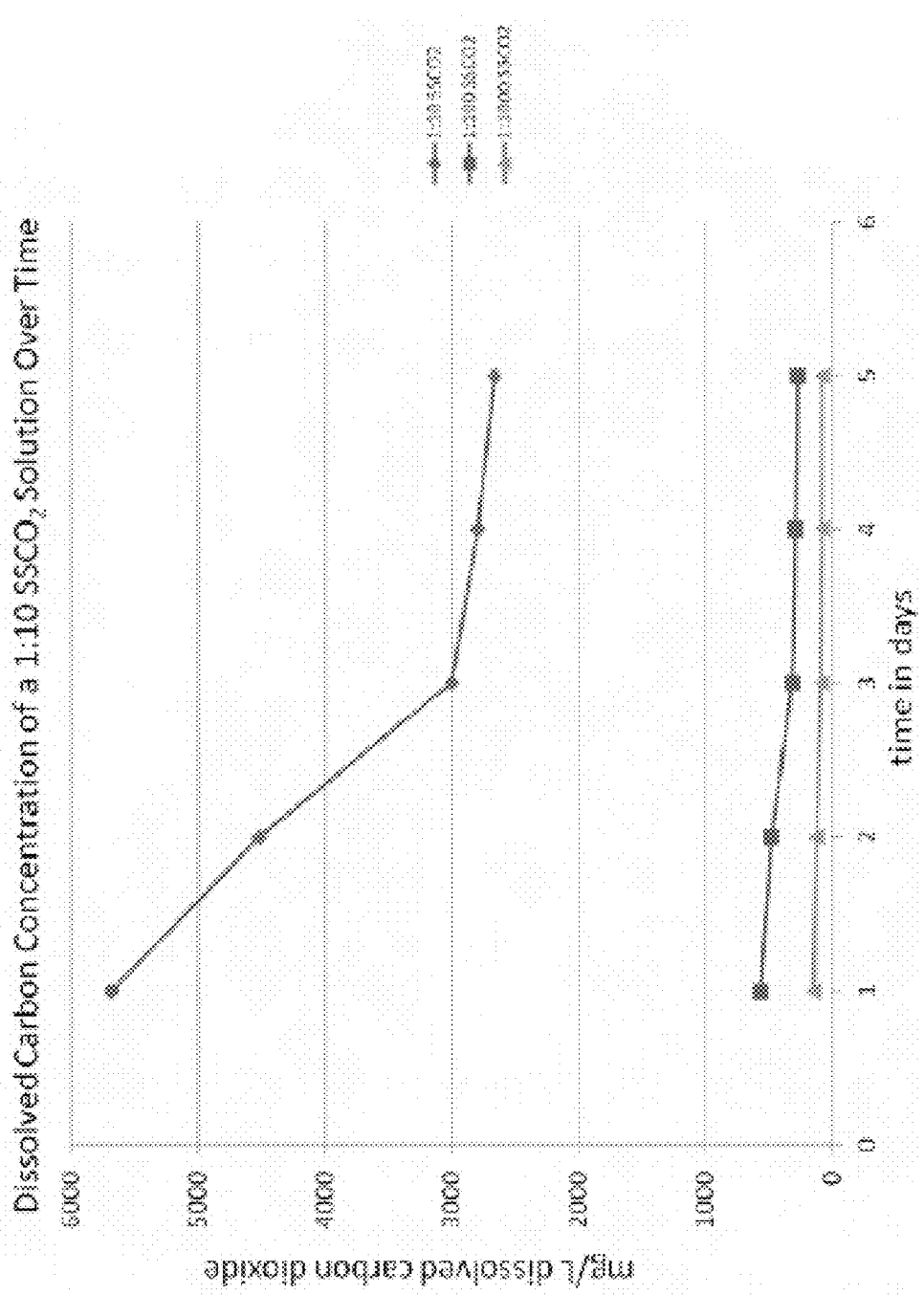
FIG. 6 shows dissolved carbon concentration of a shear-induced, $CO_2$ infused distilled water solution over time in Example 1.

The average initial concentration of the 1:10 dissolved carbon solution was measured to be 5675 ppm, or 5675 mg/L. The initial pH of each solution averaged 3.4. This unusually high concentration of dissolved carbon was confirmed by preparing fresh SSCO2 distilled water solutions and repeating the TOC measurement. The concentration of dissolved carbon dropped by about 47% within 2 days, then reached equilibrium within the following 2 days (FIG. 6). The final dissolved carbon concentration of the 1:10 SSCO2 was measured to be an average of 2655 mg/L and a pH of 3.4. As a control, distilled water was likewise measured. The TOC measurement of dissolved carbon in distilled water was 0 mg/L and the pH was measured to be 7.

Figure 7:
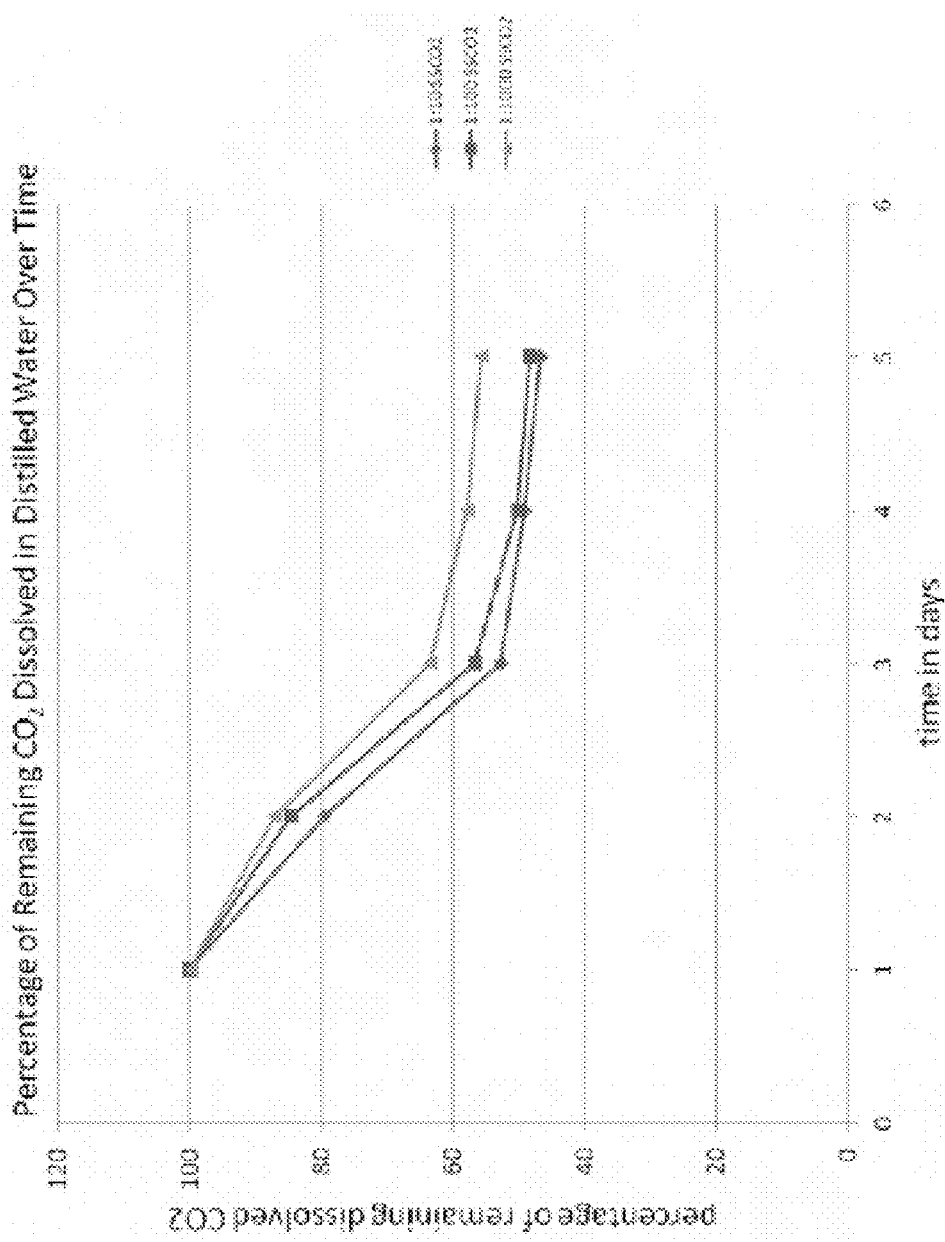
FIG. 7 shows the percentage of dissolved carbon remaining in solution over time in Example 1, which is independent of SSCO2 concentration.

The concentration of dissolved carbon in the 1:100 and 1:1000 SSCO2 solutions likewise diminished in the first 2-3 days, then reached equilibrium within 4 days (FIG. 6). The pH of each of these solutions also remained consistent throughout the tests at pH 3.4 and 3.5 respectively. These data indicate that even a small amount of dissolved CO2 in distilled water causes a drop in pH from an initial value of 7 to 3.4-3.5 and that pH alone cannot be used to calculate the concentration of dissolved carbon in distilled water when excess carbon is present. Interestingly, when the loss of dissolved carbon is expressed as a percentage of the total measured carbon, all three dilutions showed a similar pattern (FIG. 7). These data indicate that the rate of loss of dissolved carbon from a shear-induced supersaturated solution is independent of initial concentration and that the dilution of a SSCO2 solution with additional distilled water may provide an accommodating environment for excess CO2. It should also be noted these data were collected from diluted solutions which may or may not be easily extrapolated to reflect a neat SSCO2 solution.

Results Summary.

Shearing of distilled water in the presence of oxygen gas produces a supersaturated oxygen solution. Shearing of distilled water in the presence of carbon dioxide gas produces a supersaturated carbon dioxide solution that is maintained over time. The initial concentration of dissolved carbon in a SSCO2 solution diluted to 1:10 was 5675 mg/L, which then equilibrated to maintain a concentration of 2655 mg/L. The percentage loss of dissolved carbon from diluted SSCO2 solutions was consistent over the range of dilutions. Addition of dissolved carbon to distilled water causes a drop in pH from 7 to 3.4, but does not reflect the concentration of dissolved carbon when excess carbon is present.

As demonstrated by Example 1, the significant supersaturation level of carbon dioxide in solution caused by high shear processing is able to promote microorganism growth and reduce/resolve the bottleneck of insufficient $CO_2$ delivery to microorganisms, which is critical in microorganism culture and recovery of products.

Example 2

Effects of Cell Lysing Using High Shear

Cost-effective methods of disruption of the algal cell wall are fundamental to obtain higher lipid extraction efficiencies, meaning greater net energy output from the process. For this example, the effects of a method of algae cell disruption, CO2-assisted high shear, was assessed using cultured *Chlorella* sp. The combination of the actions of supersaturated micro-sized $CO_2$ bubbles and physical shearing offer a unique hybrid approach to algae cell lysing and lipid recovery. It has been unexpectedly discovered that supersaturated micro-sized $CO_2$ bubbles work in synergy with mechanical high shear action to improve cell disintegration efficiency.

Although the energy required vs. energy recovery (energy return on investment) EROI of this system was not assessed during the current testing, the system is expected to improve upon the EROI of other algae disruption technologies because it does not require pre-drying, high pressures, nor increased heat. Rather, it relies on cost-effective technologies. The efficiency and damage characteristics induced with these treatments were quantified and evaluated using direct optical microscopy and cell counting techniques. Release and recovery of intracellular lipids were also quantified.

Materials and Methods. Algae Biomass and Lipid Production.

*Chlorella* sp. (UTEX 2714) were cultivated in Bold 3N growth media and scaled to 500 L within 8" diameter vertical airlift photobioreactors exposed to a daily 18/6 cycle of artificial illumination. Cell culture density was measured daily by dry cell weight. Nitrogen was limited once the culture reached 1.8 g/L to stimulate lipid accumulation within the cells. Once the culture density reached 2 g/L, 10% of each culture was tested as "dilute" culture while the remaining 90% of the culture was concentrated by centrifugation to a final "concentrate" of 12-15 g/L pumpable slurry. Algae lipids were extracted using a modified Folch method, quantified gravimetrically, and expressed as % total lipid/dry cell weight.

CO2-Assisted High Shear Algae Cell Disruption Set Up and Test Matrix.

Figure 8A:
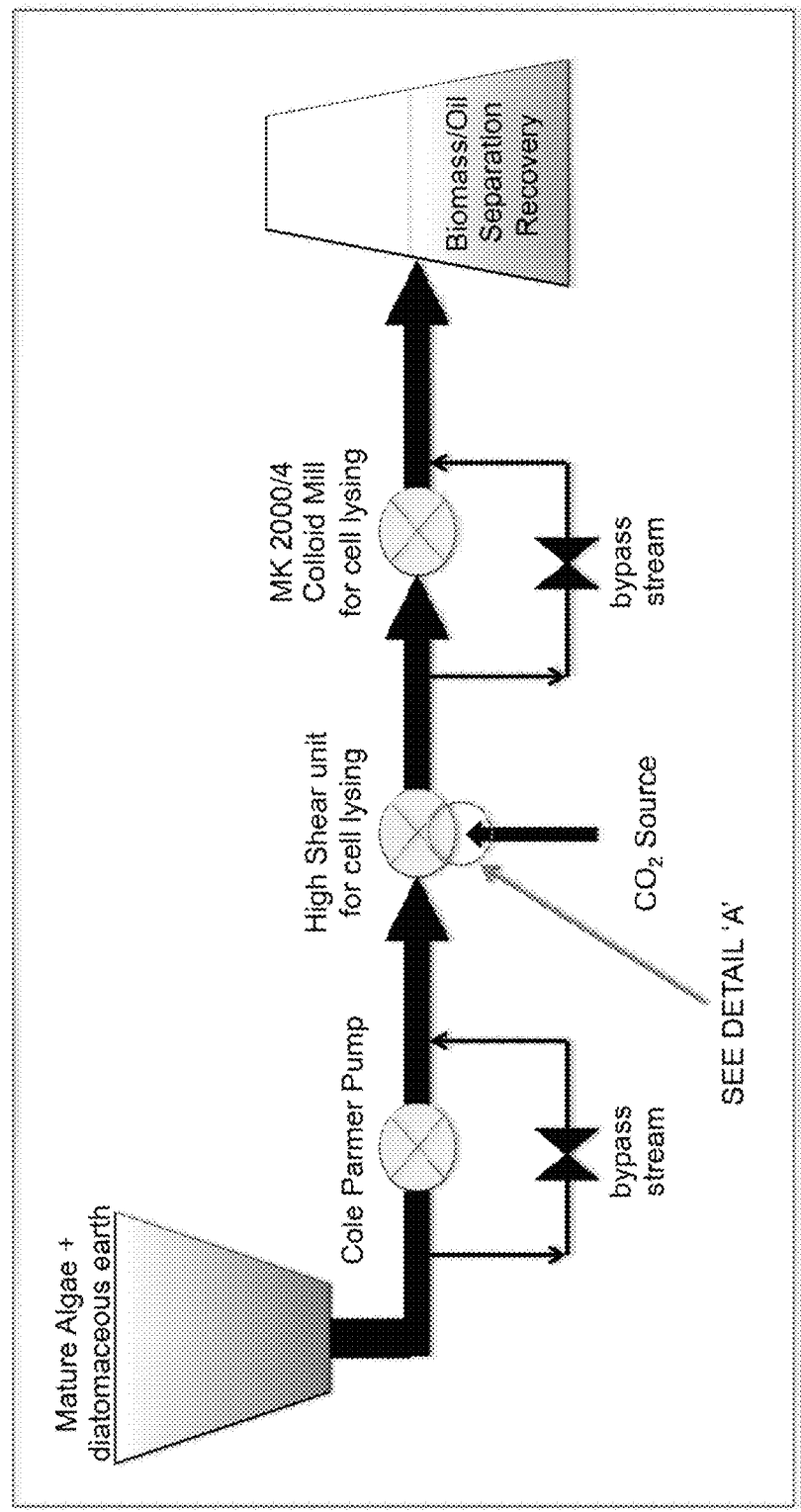
FIG. 8a illustrates a CO2-assisted high shear algae cell disruption flow diagram, according to an embodiment of this disclosure.
Figure 8B:
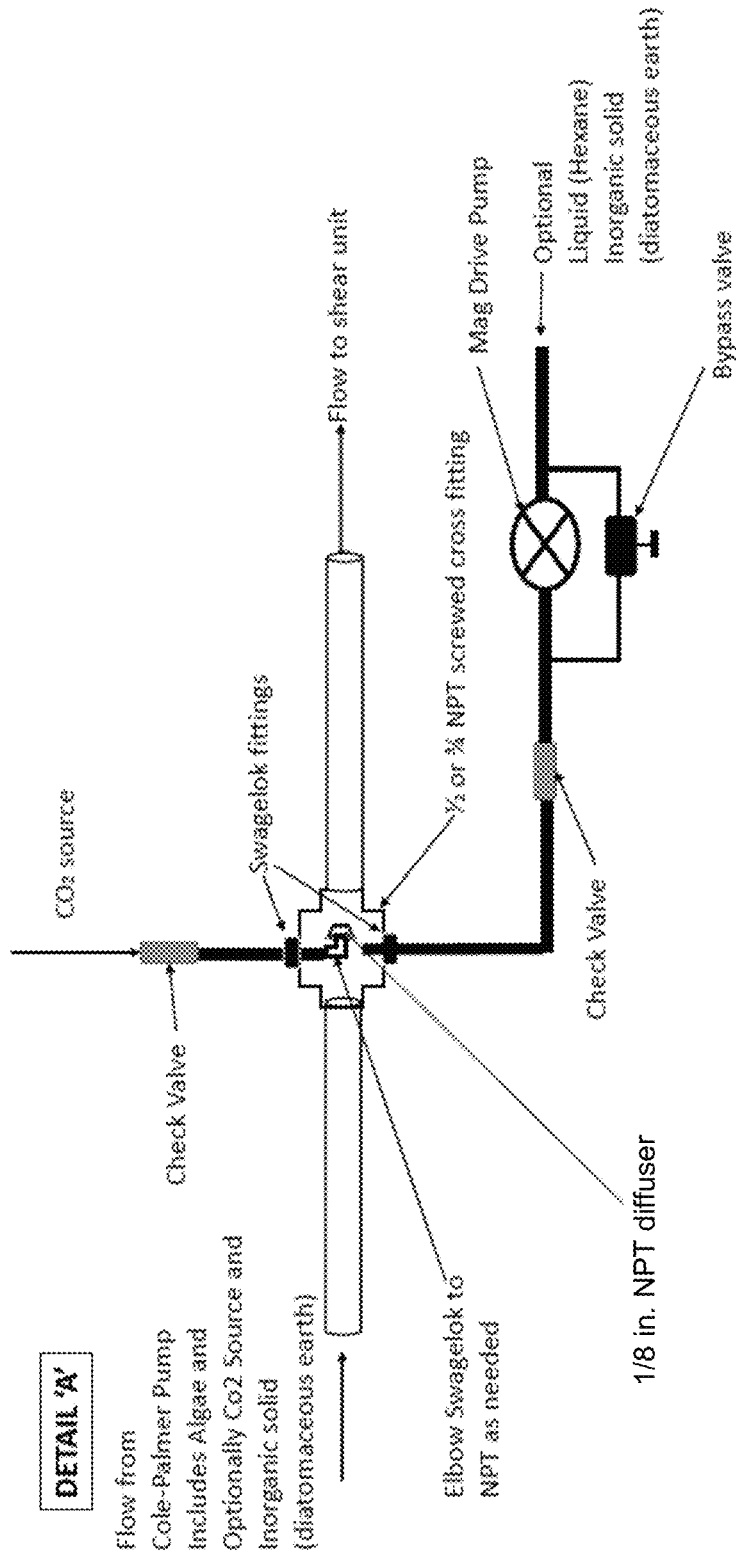

The process flow for CO2-assisted high shear algae cell disruption is shown in FIG. 8a. Biomass slurry sample flow and processing was initiated as follows: the fluid flow pressure of dilute or concentrated algal slurry through the system was initiated at ~80 psi and subsequently increased to 85-105 psi. The high shear unit was then turned on and maintained at a rotational speed of 15,000 or 26,000 rpm as indicated in the results section. Diffused CO2 (FIG. 8b) was introduced into the system at the shear unit an initial pressure of 80 psi, then adjusted to 85-105 psi to reduce sample sputtering from the collection nozzle. When applicable, the colloid mill was turned on. In some test cases, the back pressure to the shear unit was increased in increments of 20 psi from 0 psi to 80 psi. Once the target test parameters were met, processed samples were collected in Erlenmeyer flasks for subsequent cell disruption and lipid release analyses.

A matrix of test conditions were applied to the algae samples. Matrix variables included fluid flow pressure entering the high shear unit (0, 80-150 psi), back pressure to the high shear unit (0-80 psi), CO2 pressure entering the high shear unit (0, 80-105 psi), and dilute (2 g/L DCW) vs. concentrated (12-13 g/L) *Chlorella* algae.

Quantification of Cell Disruption.

The effectiveness of each treatment was qualitatively visualized by brightfield microscopy (10×-40×), and quantified by measuring the fraction of physically disrupted cells (Spiden, 2013). ImageJ, a public-domain image processing and analysis software, was used to ensure consistency in cell counting by minimizing variability in analysis between samples. Measurements of the total area occupied by cells were used to verify the intact cell counts. This was particularly useful for samples with cell clumping, typically observed in samples that had been homogenized at higher pressures. All imaging was performed using an AmScope B120C-E1 Siedentopf Binocular Compound Microscope with a 1.3 MP digital camera. Cell counts were compared to unprocessed (flowed through the system but no shear, mill, or CO2) algae from the same batch. Cell viability was assessed using a standard XTT viability assay, which measures mitochondrial enzymatic activity.

Quantification of Recovered Extracellular Lipids Following Shear Processing.

Lipids released as a result of cell rupture were quantified by sweeping the extracellular medium by inversion with 10% hexane for 30 seconds. The hexane layer containing released lipids was phase partitioned and recovered following centrifugation of the sample. Following hexane distillation, the recovered dry lipids were quantified grayimetrically and expressed as the % of released lipids/dry cell weight of biomass.

System Operation and Cleaning.

Prior to activating the system for each set of tests, warm tap water was cycled through the system. Once flow was established, each component (high shear unit, CO2 gas flow, colloid mill) of the system was turned on. The system was deemed fully operational if: 1) the fluid flow through the system was unrestricted, 2) the shear and colloid mill units reached full rotational speed, 3) all gas and fluid flow pressures were achieved, and 4) the pH of the final water solution dropped to expected levels, typically from pH 8-9 to pH 5-6. The system was then turned off, the remaining water in the system was replaced with algae slurry, and the process was repeated prior to adjusting test parameters and data collection. Following each set of tests, any remaining algae slurry in the system was replaced with warm tap water, which was circulated through the system for 30 minutes prior to shutting the system down. In some cases, a thin opaque film lining the clear tubing in the system was observed in the following days, suggesting that a biofilm may have developed within the system. This observation was further supported when it was also noted that the fluid flow through the system appeared to be slightly restricted upon start-up. In these cases, isopropyl alcohol was circulated through the system, followed by a citrate solution, until the fluid flow was restored.

Figure 9:
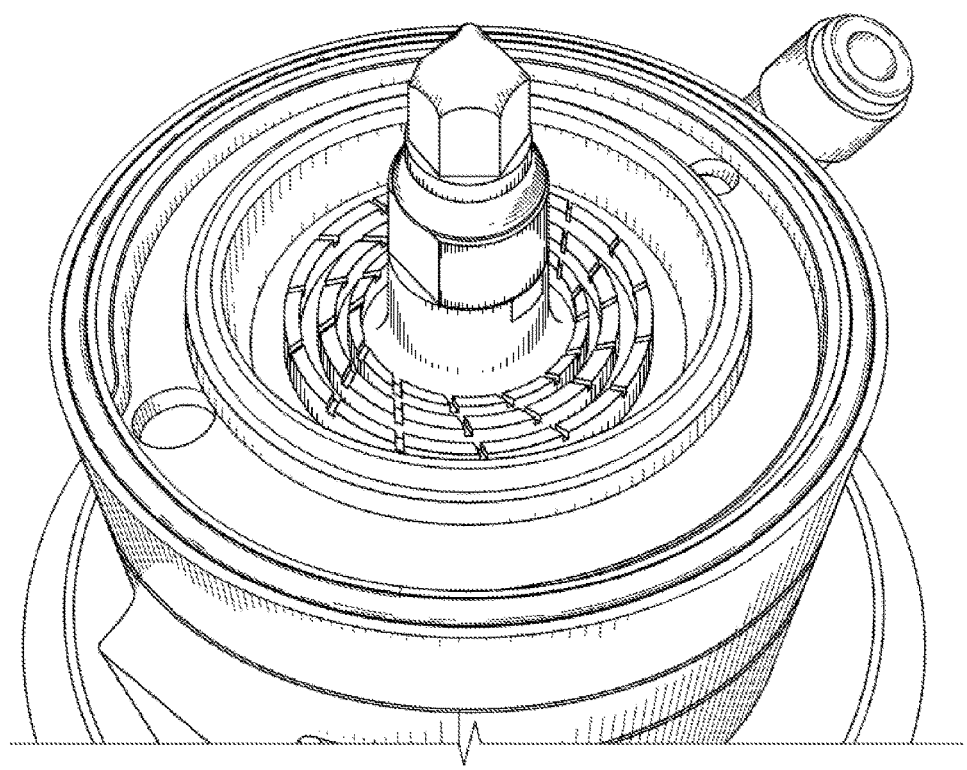
FIG. 9 shows the particulates observed within the rotor of the high-shear unit in Example 2.

Following system operation using diatomaceous earth, the restriction in fluid flow was even more pronounced and in some cases, the high shear unit became non-operational and displayed an Error F50 message (rotor shaft blocked). Cleaning the flow path with the isopropyl alcohol-citrate method was insufficient to restore fluid flow or shear unit operation. Instead, the system required disassembly, direct soft brush cleaning, and reassembly before the system could be restored to and operational condition. The disassembly included the plumbing emanating from the mag lev pump to the shear unit and the rotor shaft of the high shear unit (FIG. 9). Once the system was manually cleaned and reassembled, operation was restored and testing was resumed. The issues with restricted fluid flow caused by the addition of diatomaceous earth may become less relevant as the system is scaled up to a commercial scale, although biofilm formation may still occur.

Results and Discussion.

In order to identify the operating conditions that maximized algae cell disruption, a test matrix in which individual parameters were varied one at a time was created. Testing started with the basic CO2-assisted high shear system alone, followed by the addition of diatomaceous earth (silica remnants of algae diatoms) to enhance local shearing, and finally by the downstream addition of a colloid mill.

CO2-Assisted High Shear Algae Cell Disruption.

Initially, dilute and concentrated *Chlorella* sp. cells were processed through the CO2-assisted high shear unit at 15,000 rpm without additional exposure to the downstream colloid mill. In our previous work, we had shown that the infusion of excess CO2 into the process stream supersaturates the effluent solution with CO2 and causes a significant drop in slurry pH. Since the infusion of excess CO2 into the shear unit was integral to the current cell disruption process flow, we again monitored pH throughout these tests. Along with changes in pH, the fluid flow pressures at various points throughout the process flow path were systematically changed one at a time in order to identify the operating parameters that maximized algae cell rupture, which was qualitatively evaluated microscopically following each sample run. To quantify the percentage of cells disrupted (lysed) following some test runs, cell counts were also performed on equal volumes of processed unprocessed control cells from the same batch. The pH of the processed slurry dropped by ~35%, indicating that the infused CO2 was supersaturated into the buffered algae slurry. However, none of the initial operating test conditions, 80-150 psi (shear influent), 80-105 psi (CO2), 0 psi back pressure to the shear unit caused any significant cell disruption. Others have reported robust mechanical (blender) shear-induced algae lysis for algae exposed to the shearing forces for 20 minutes. For the current tests, the shearing mechanism differs in three important ways: algae slurry flows through an inline dual-stage particle distribution rotor, CO2 is directly fed into the process flow stream, and exposure to shear forces in this system is 1-2 seconds. Given the short exposure time and microscopic size of the individual cells (3-5 µm), Following an initial evaluation, the culture was re-processed through the unit a second time ($2^{nd}$ pass) and samples were again imaged immediately. Although not significant, some cell disruption was visualized by the presence of additional cell debris and a 4% decline in cell number compared to controls. A $3^{rd}$ pass of the slurry through the system did not cause additional cell disruption, suggesting that additional processing beyond a single pass may not be useful (for *Chlorella*).

Figure 10:
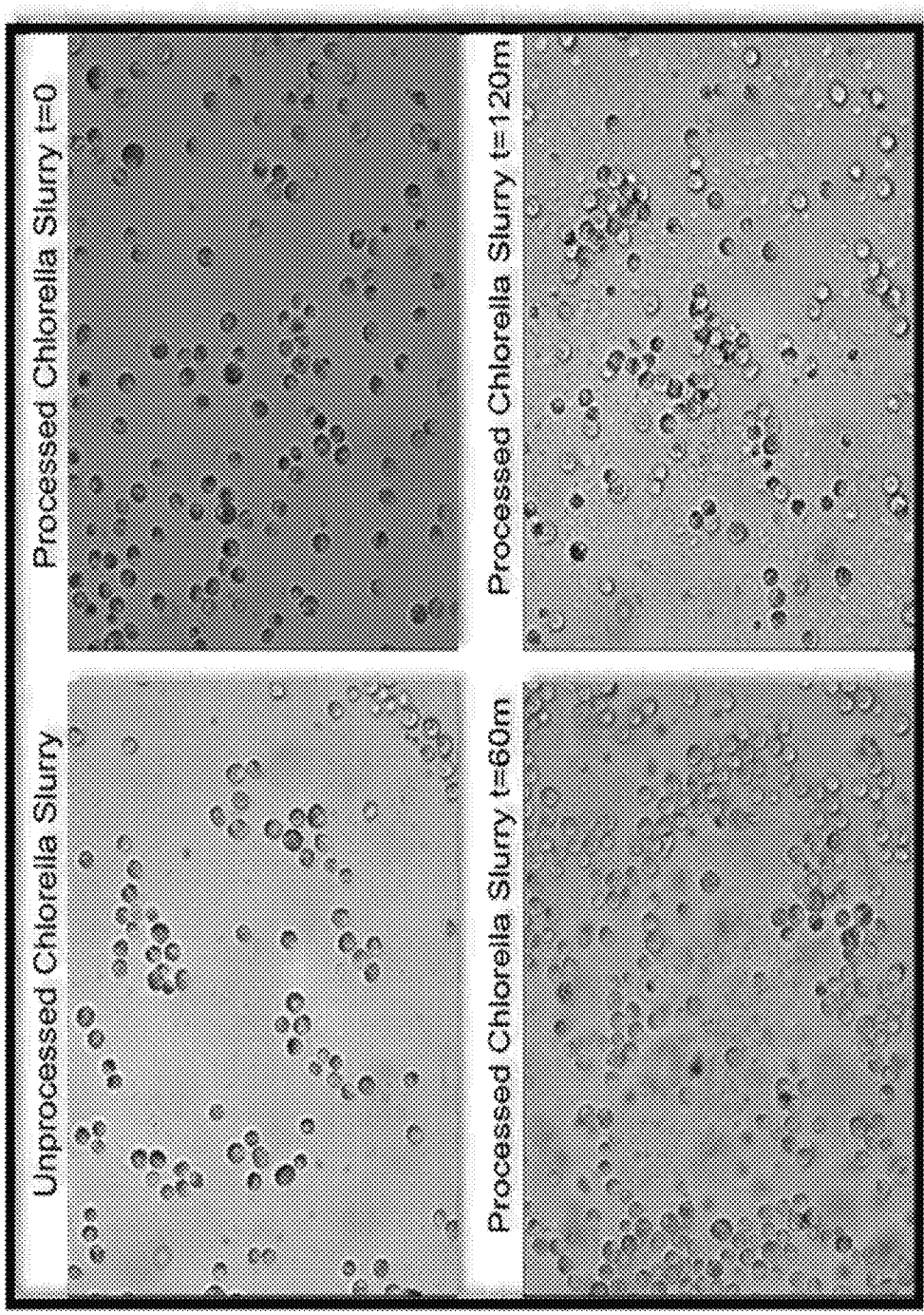
FIG. 10 shows time dependent effects of SSCO2-assisted high shear lysis of algae cells observed by microscopy in Example 2.

Because the slurry is supersaturated with CO2 as it is processed through the system, and excess CO2 is lethal to many species of algae, the effects of prolonged exposure to excess CO2 were likewise evaluated. An additional 60-minute incubation following processing revealed striking differences between these samples and freshly processed or control samples. Significantly more cellular debris was visualized microscopically and on a macroscopic scale, the color of the 1st pass culture changed from a bright kelly green to a greenish-gray. These data indicate not only cellular compromise, but that the phytol tails of chlorophyll molecules within the slurry had been cleaved, changing the overall optical character of the slurry. This effect was further exaggerated after a 120 minute waiting period (FIG. 10).

These tests were repeated with thawed (non-viable) algae concentrate (14% w/v) with very different results. There was no increased cellular debris visualized following either the 1st and 2nd pass, nor was there any increased cell disruption following an additional 60 m or 120 m incubation period. Together, these data suggest that the increased cell disruption following additional incubation in the supersaturated CO2 slurry was caused by the chemical actions of excess CO2 rather than mechanical shearing. Although CO2-induced cell disruption appears to be a somewhat effective method to compromise a small population of viable *Chlorella*, the optical changes that occurred with this process also suggest that unwanted chemical degradation to targeted co-products may also be occurring.

Figure 11:
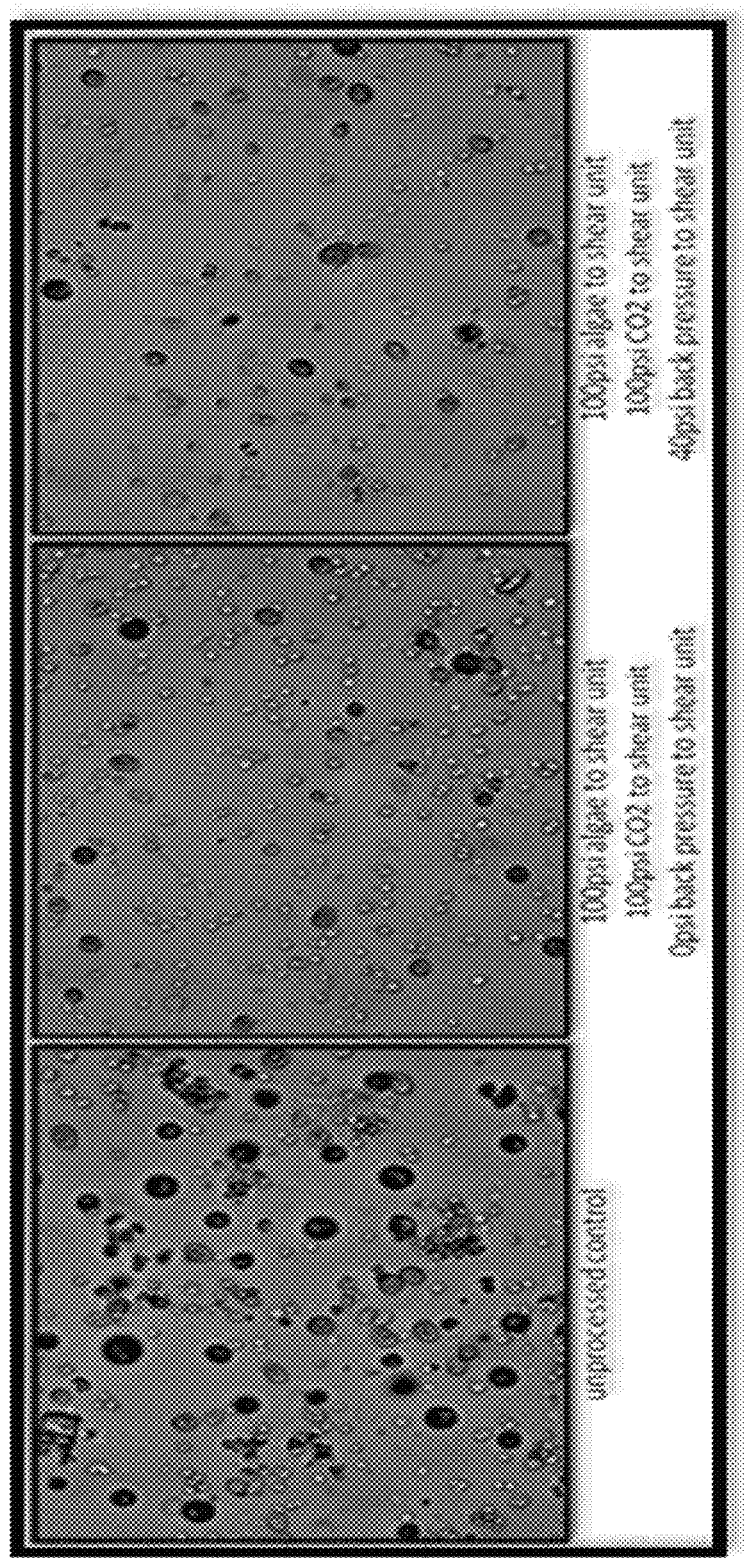
FIG. 11 shows representative images of processed algae slurry through the CO2-assisted high shear unit in Example 2.

As a means to increase the CO2 cavitation effects within the shear unit, the back pressure to the shear unit was incrementally increased from 0-80 psi. The shear unit influent pressure was held at 100 psi and the CO2 gas pressure to the shear unit was likewise held at 100 psi. At 0 psi back pressure to the shear unit, the slurry exiting the process flow collection nozzle could be described as "sputtering and spitting" and minimal lysis was observed. Applying back pressure to the unit (20, 40, 60 and 80 psi) caused both decreased sputtering and increased cell disruption, with the greatest effects at 20 psi and 40 psi (FIG. 11). At these back pressures, fluid flow exiting the collection nozzle was restored to a consistent stream. Cellular debris was estimated to be the result of 30% cell lysis, and was quantified by cell counts to be 27%. Following an additional 2 h incubation period, total cell lysis increased to 73%.

Summary of CO2-Assisted High Shear Algae Cell Disruption.

The effects of all fluid and gas flow variables tested through the mechanical shearing (15,000 rpm) unit on viable dilute *Chlorella* cells were negligible. Although immediate cell disruption was not apparent, viable *Chlorella* cells that were further incubated in the processed supersaturated CO2 slurry were disrupted in a time-dependent manner. Cell disruption caused by an extended exposure to excess CO2 caused additional chemical reactions that negatively impact chlorophyll. Applying a back pressure of 20-40 psi to the shear unit enhanced the immediate effects of the CO2-assisted high shear process.

Diatomaceous Earth+CO2-Assisted High Shear Algae Cell Disruption.

Diatomaceous earth consists of fossilized remains of diatoms, a type of hard-shelled (silica) algae, and is used commercially as a mild abrasive. Abrasive materials that are similar in size to the individual algae cells (~5 μm) can enhance cell shearing. As part of the testing matrix, 0.01-1% w/v of diatomaceous earth (7-10 μm) was homogenized into the algae slurry prior to entering the process stream. The rotational speed of the shear unit was also increased from 15,000 rpm to 26,000 rpm. A matrix of tests was conducted, with 100 psi influent, 100 psi gas pressure, and 40 psi back pressure to the shear unit yielding the best results. Initially, a 1% (w/v) solution was added to the algae slurry and processed through the system. This caused the system, including the plumbing and the shear unit rotor shaft to clog. Following manual cleaning, the concentration of diatomaceous earth was reduced to 0.01% (w/v). The addition of 0.01% DE to the algae slurry processed under the matrix test conditions yielded similar cell lysing results as controls with no DE. However, the *Chlorella* cells that were originally present in clusters were separated into single cells following a first pass through the shear unit. A second pass of the 0.01% DE SSCO2 algae slurry through the system did not improve immediate cell rupturing. When the concentration of DE was increased to 0.1%, the lysing efficiency from a single pass improved significantly. Like the result using a 0.01% DE supplement, clusters of algae cells were separated into single cells and the percentage of lysed cells following a single pass was 54%. Further, an oily sheen was detected on the surface of the processed slurry, indicating the release of intracellular lipids from the algae cells within the process slurry. This result could not be repeated, however, as the system clogged repeatedly using a DE concentration of 0.1%. This 54% increase in lysing may have been a single result of the accumulated DE in the system, and when the system was cleaned, this effect was lost.

Summary of Diatomaceous Earth+CO2-Assisted High Shear Algae Cell Disruption.

Increasing the rotational speed of the shear unit from 15,000 rpm to 26,000 rpm (maximum) did not cause additional cell disruption over controls (15,000 rpm, 100 psi influent, 100 psi CO2, 40 psi back pressure). Addition of 0.01% diatomaceous earth to the process slurry caused algae clusters to separate, but did not increase cell disruption under any condition over controls following two passes through the system. Addition of 0.1% diatomaceous earth to the process slurry caused a 24% increase in cell disruption (54%) over controls processed without DE (30%), likely due to excess DE in the system.

0.01% Diatomaceous Earth (DE)+CO2-Assisted High Shear (SSCO2)+Colloid Mill (CM) Algae Cell Disruption.

Figure 12:
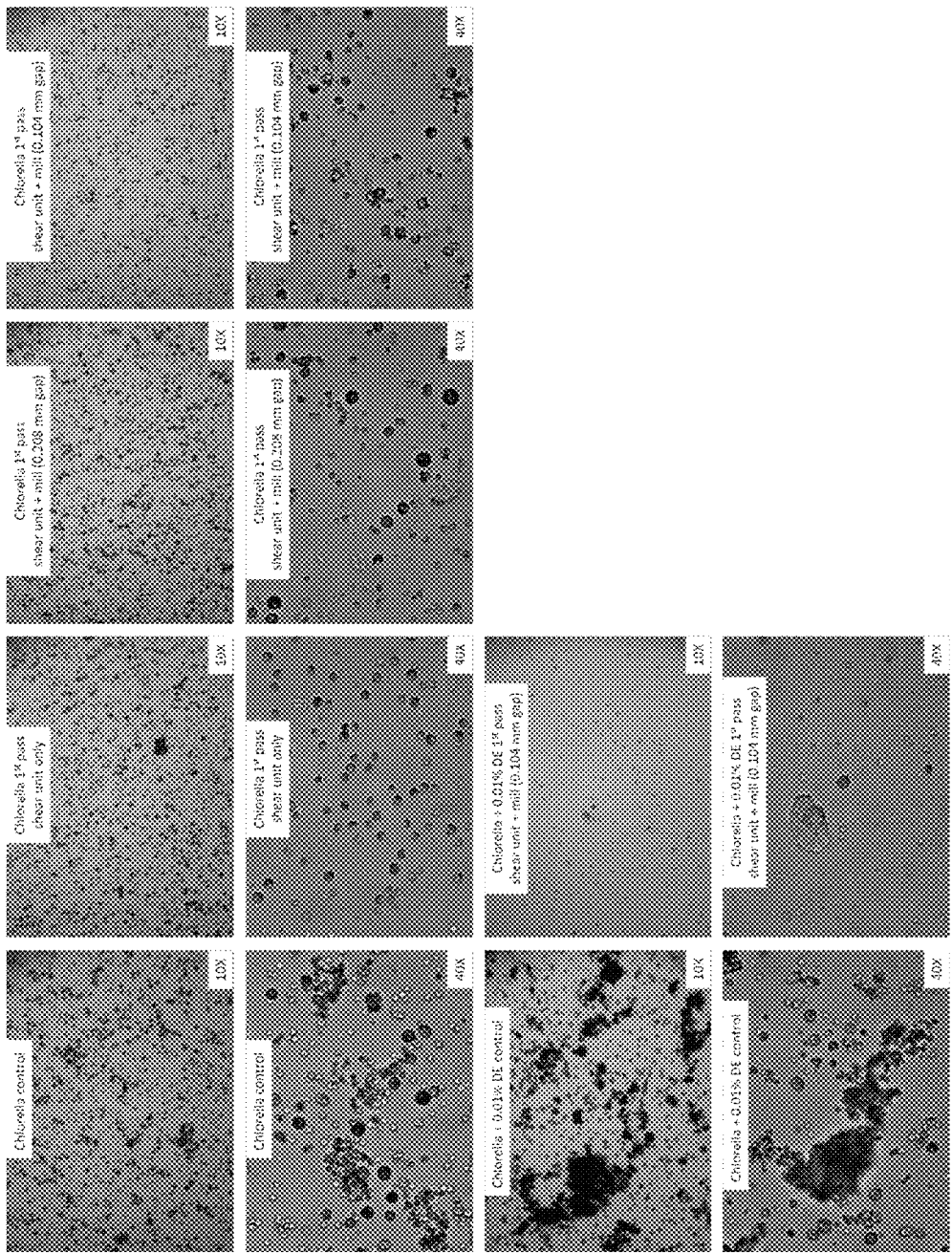
FIG. 12 shows representative microscopic images of control and processed (SSCO2-shear-colloid mill) algae slurry in Example 2.

A colloid mill is a machine that is used to reduce the particle size of a solid in suspension in a liquid, or to reduce the droplet size of a liquid suspended in another liquid. Colloid mills work on the rotor-stator principle: a rotor turns at high speeds (2000-18000 RPM). The resulting high levels of hydraulic shear applied to the process liquid disrupt structures in the fluid. Colloid mills are frequently used to increase the stability of suspensions and emulsions, but can also be used to reduce the particle size of solids in suspensions. Higher shear rates lead to smaller droplets (~1 μm) that are more resistant to emulsion separation. For the current application, the goal was to break ~3-10 nm-sized algae into fragments and release commercial co-products (oil) into the surrounding medium. Therefore, an MK/2004 Colloid Mill was introduced as an additional shearing mechanism downstream of the CO2-assisted high shear unit. Primary factors that influence cell shearing include the gap distance between rotors and the rotation speed. Initially, the rotational speed was set to 3160 rpm and the gap was set to 0.208 mm. The pressure of the slurry entering the shear unit was set to 100 psi, CO2 gas pressure was set to 95 psi, and the back pressure to the shear unit was set to 40 psi. These conditions produced a smooth fluid flow exiting the sample collection nozzle and the lowest pH of the processed slurry. Process controls included algae slurries without DE, and slurries with 0.01% DE but processed through the colloid mill in the "off" mode. In this case, clusters of *Chlorella* cells were again reduced to single cells and the reduction in cell count was ~35%. When the colloid mill gap was decreased to 0.104 mm and no DE was added to the process slurry, lysing improved by 5%. However, when 0.01% DE was added to the process stream with a colloid mill gap width at 0.104 mm, widespread debris was visualized and the total number of cells decreased by 81% compared to unprocessed controls from the same batch slurry (FIG. 12). The total intracellular oil available within this batch of algae slurry was calculated to be 16.7%. A small amount of oil can often be detected in the extracellular medium as a result of the solvent sweep method to recover lipids in the process medium. In this case, the percentage of oil in the extracellular medium was calculated to be 1.8%.

Figure 13:
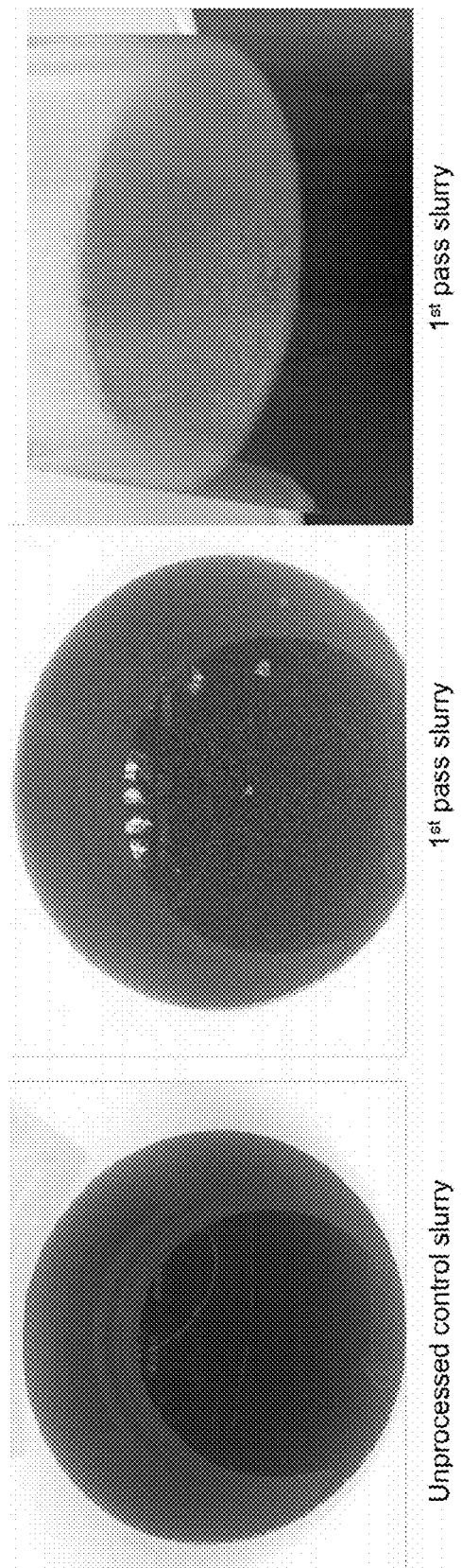
FIG. 13 shows the oily surface observed on CO2-assisted high shear processed algae slurry in Example 2.

Following the first pass of the slurry plus 0.01% DE through the high-shear unit and colloid mill with the gap adjusted to 0.104 mm, the percentage of extracellular oil increased to 12.2%. In other words, this process (0.01% Diatomaceous Earth (DE)+CO2-assisted High Shear (SSCO2)+Colloid Mill (CM), i.e., DESSCO2CM process) caused the release of 62% of the intracellular oil into the extracellular medium, some of which could be observed at the surface of the processed slurry (FIG. 13). The difference between cell lysis (81%) and lipid release (62%) may be explained in part by noting the species of lipids that were made readily available by the current processing parameters. Non-GMO *Chlorella* triglycerides (~2-20%) are typically packaged within cells as easily accessible lipid bodies whereas phospholipids (30-85%) are embedded within membranes and can be resistant to recovery by sweep solvents. The release of 62% of total lipids indicates that the current process method significantly disrupts cellular membranes containing phospholipids allowing their recovery from a single solvent sweep.

These tests were conducted at a bench scale. Although up to 81% of algae cells were disrupted, some operational challenges were noted. Under all of the combinations of parameters tested, the addition of diatomaceous earth appeared to be necessary to increase lysing efficiency.

Summary of Diatomaceous Earth+CO2-Assisted High Shear+Colloid Mill Algae Cell Disruption.

The addition of the downstream colloid mill with the gap set to 0.104 mm improved algae cell lysis by ~50%, for a total of 81% of cells ruptured. The following parameters yielded 81% cell lysis and 62% lipid release: 0.01% DE; IKA Magic high shear unit, 26,000 rpm; colloid mill, 3160 rpm, 0.104 mm gap; 100 psi influent pressure (to the shear unit); 95 psi CO2 gas pressure (to the shear unit); 40 psi back pressure (to the shear unit). DE accumulates within the small diameter tubing in the system over time and decreases fluid flow and lysing efficiency, and eventually leads to severe blockage that requires manual cleaning. Larger scale systems may be less susceptible to DE accumulation. Given the low energy requirements for this system, this process could significantly improve the energy balance for production of algal biofuels, especially if it can be synergistically combined with a vacuum to efficiently harvest released algal cell lipids.

Example 3

Gas-Assisted High Shear Cell Lysing

Flow-through algae cell disruption testing was demonstrated in Example 2 using a $CO_2$-infused high-speed, high-pressure rotor-stator homogenizer (HSPH) and colloid mill homogenizer (CMH). The testing showed that the infusion of pressurized $CO_2$ into the HSPH and immediate exposure to the CMH are unique and important drivers of the cellular disruption efficiency. A proposed mechanism states that the rapid infusion of $CO_2$ into the algal cells causes intracellular disruption and cellular swelling, and the immediate subsequent exposure to shear forces significantly enhances cellular disruption and product recovery. Although energy balance was not examined, the algae were compromised in a single pass, and therefore, the required energy input into the system is expected to be far less than current non-$CO_2$ shearing technologies that require multiple passes.

The $CO_2$-assisted shearing system was likewise tested using yeast as the bio-feedstock. After replacing $CO_2$ with $O_2$, significant yeast lysis was observed.

Materials and Methods. Yeast Biomass Production.

A genetically engineered strain of yeast, *Yarrowia lipolytica*, provided by Dr. Hal Alper, University of Texas. Baker's yeast, *Saccharomyces cerevisiae* were fermented in 37° C. dH2O supplemented with 20% D-glucose and 2% bacto yeast extract within 2 L sterilized glass bioreactors. Culture density was recorded by absorbance at 600 nm. Cultures near the end of the exponential phase of growth were used for testing.

$CO_2$-Assisted High Shear Algae Cell Disruption Set Up and Test Matrix.

The process flow for $CO_2$-assisted high shear yeast cell disruption is shown in. Biomass slurry sample flow was initiated as follows: the fluid flow pressure of dilute or concentrated yeast slurry through the system was initiated at 100 psi. The high shear unit was then turned on and maintained at a rotational speed of 26,000 rpm. Diffused $CO_2$ was introduced into the system at the shear unit an initial pressure of 80 psi, then adjusted to 95 psi to reduce sample sputtering from the collection nozzle. The colloid mill was then activated. In some test cases, the back pressure to the shear unit was increased in increments of 20 psi from 0 psi to 40 psi. Once the target test parameters were met, processed samples were collected in Erlenmeyer flasks for subsequent cell disruption analyses.

$O_2$-Assisted High Shear Yeast Cell Disruption Set Up.

The process flow for $O_2$-assisted high shear yeast cell disruption was identical to the $CO_2$-assisted high shear system except that the $CO_2$ was replaced with $O_2$ gas infusion.

Quantification of Cell Disruption.

The effectiveness of each treatment was qualitatively visualized by brightfield microscopy (10×-40×), and quantified by measuring the fraction of physically disrupted cells. ImageJ, a public-domain image processing and analysis software, was used to ensure consistency in cell counting by minimizing variability in analysis between samples. Measurements of the total area occupied by cells were used to verify the intact cell counts. This was particularly useful for samples with cell clumping, typically observed in samples that had been homogenized at higher pressures. All imaging was performed using an AmScope B120C-E1 Siedentopf Binocular Compound Microscope with a 1.3 MP digital camera. Cell counts were compared to unprocessed (flowed through the system but no shear, mill, +/−$CO_2$ or $O_2$) yeast from the same batch.

Results and Discussion. $CO_2$-Assisted High Shear Yeast Cell Disruption.

In order to identify the operating conditions that maximized yeast cell disruption, a test matrix in which individual parameters were varied one at a time was created. Yeast was initially processed through the $CO_2$-assisted high shear, high-pressure homogenization (HSPH) system using the parameters that were previously observed to maximize algae cell disruption (shear unit speed, 26,000 rpm; colloid mill, 3160 rpm, gap 0.14 mm; 100 psi shear unit influent; 95 psi $CO_2$ to the shear unit; 40 psi back pressure to the shear unit). No diatomaceous earth was used in the yeast process testing.

Despite using the same conditions that caused ~80% of processed *Chlorella* cells to lyse, no significant cell lysis was observed for processed yeast cells after one, two, or three processing passes. Increasing the back pressure to the shear unit likewise had no significant effect on yeast cell lysis. The differences between algae and yeast cellular respiration requirements ($CO_2$ vs $O_2$) may explain this result. Algae readily take up $CO_2$ in the form of $CO_2$ gas or dissolved carbonate and release $O_2$ as a byproduct of cellular respiration. In contrast, yeast preferentially take up $O_2$ by gradient diffusion across its membrane and releases $CO_2$ as a byproduct of cellular metabolism. When there are two gases separated by a permeable membrane (like the cell/plasma membrane), the gas will move across the membrane from the high concentration environment, in this case the gas-infused shear unit, to the low concentration of that gas (the intracellular compartment) until the concentrations on each side equalize. As long as there is always a lower concentration of oxygen inside the cell than outside the cell, oxygen will continuously diffuse into the cell. Isenschmid et al. (1995) reported that yeast exposed to 60 bar (870 psi) $CO_2$ for 15 minutes were not lysed; rather the yeast cells appeared intact but were rendered non-viable likely due to $CO_2$ toxicity. For the current tests, the goal was cellular destruction that facilitated lipid extraction and recovery, and therefore additional testing using $CO_2$ as the infusion gas was discontinued, and replaced with $O_2$ gas.

Figure 14:
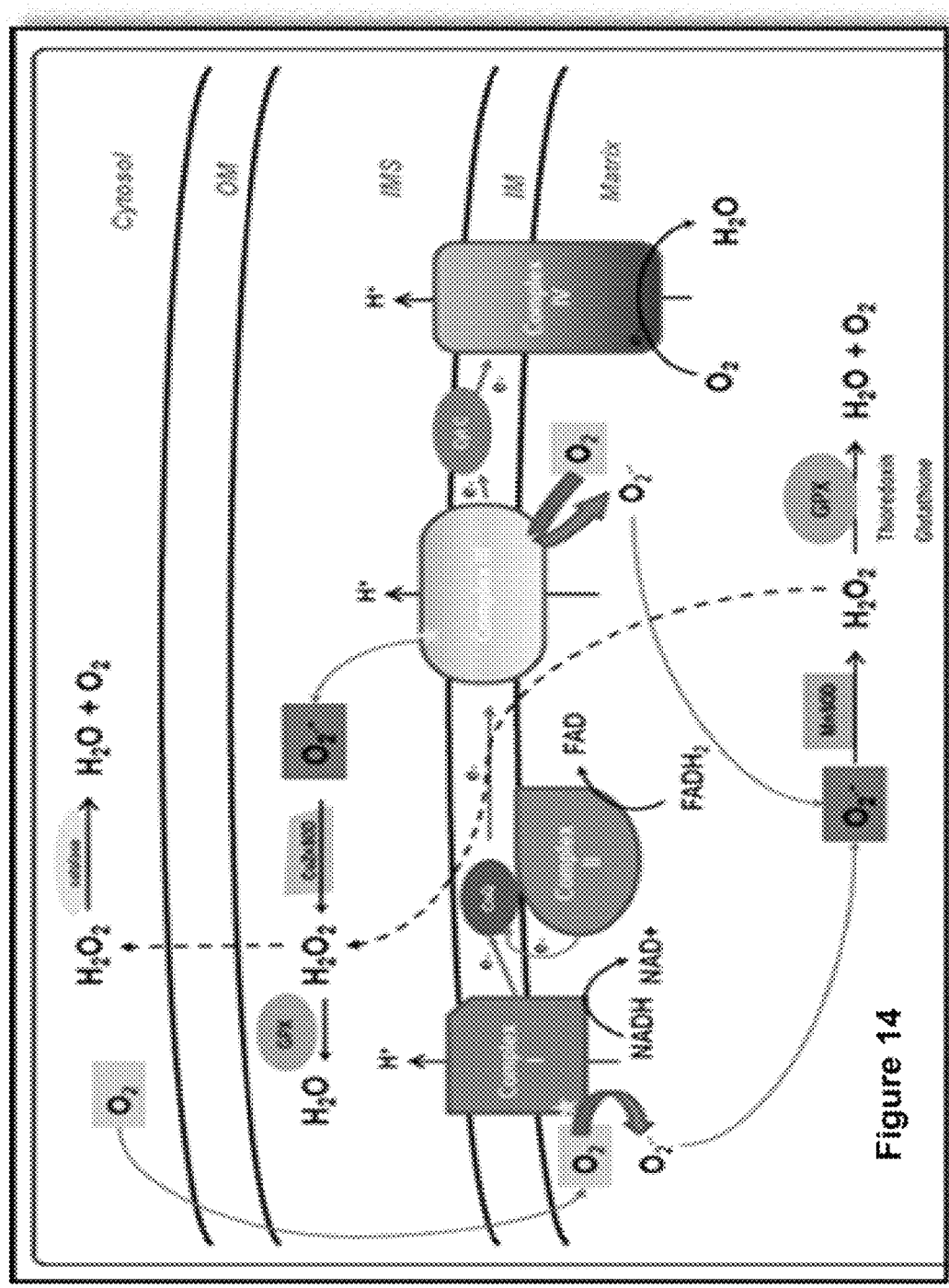
FIG. 14 illustrates excess O2 leading to reactive oxygen species (ROS) generation and cell death within yeast cells in Example 3.

Substituting $O_2$ as the gas infused into the shear mechanism was predicted to have advantages over $CO_2$-assisted shearing. Firstly, yeast cells preferentially take up $O_2$ gas. Because yeast efficiently metabolize $O_2$, the concentration of $O_2$ within the intracellular compartment remains low and the concentration gradient for $O_2$ diffusion into yeast cells is comparatively large. Second, the supersaturating concentration of $O_2$ within the shear unit forces excess $O_2$ into the cells. Excess $O_2$ intake within yeast leads to the generation of reactive oxygen species within the intracellular compartment, which in turn leads to cell expansion and eventually cell death (FIG. 14). The expanded membranes of $O_2$-supersaturated yeast cells were predicted to have less localized tensile strength and therefore more susceptible to shearing forces.

O2-Assisted High Shear Yeast Cell Disruption.

Figure 15:
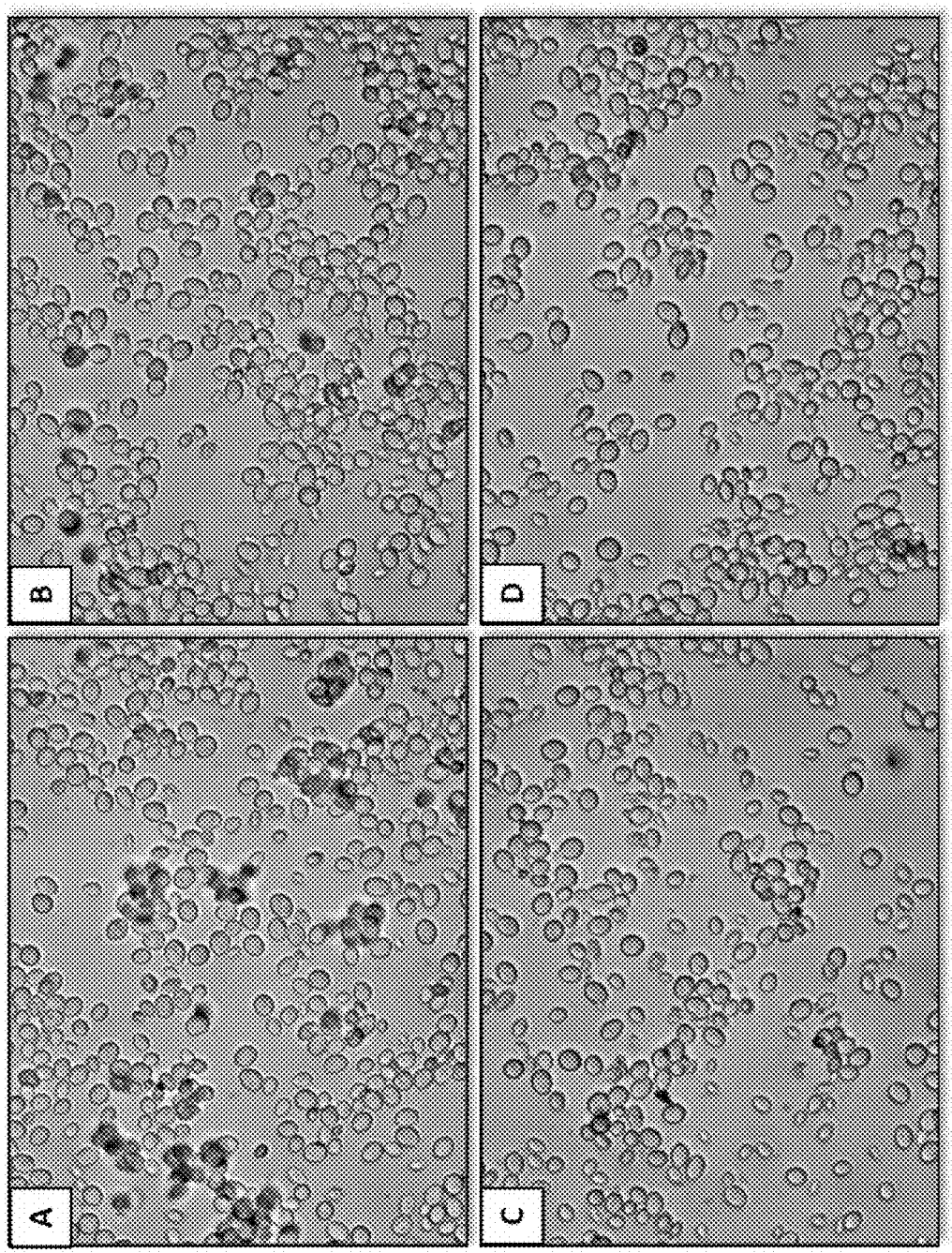
FIG. 15 shows representative microscopic images (40×) of unprocessed control yeast (A), 1st pass samples exposed to 0 psi back pressure (B), 20 psi back pressure (C), and 40 psi back pressure (D) in Example 3.
Figure 16:
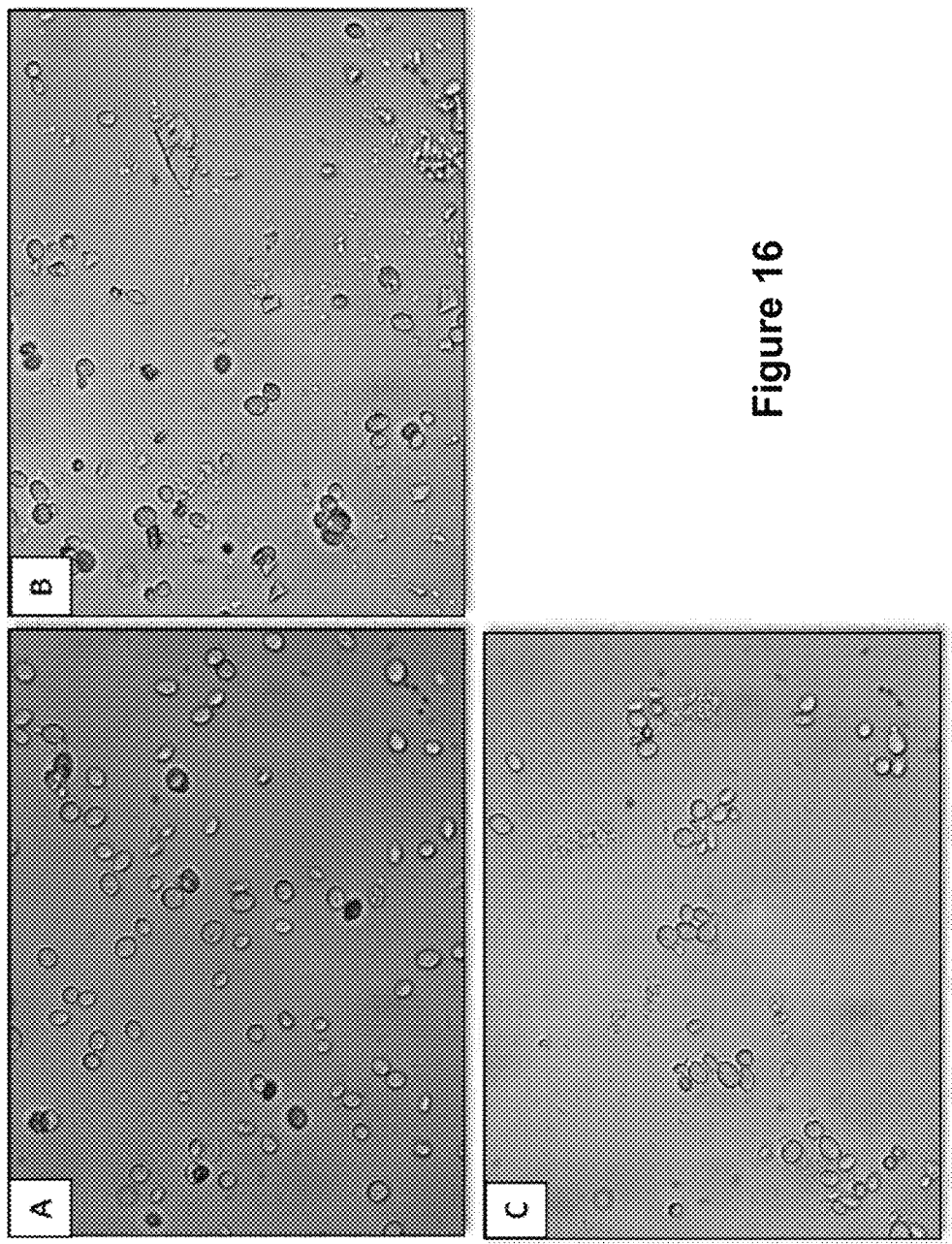
FIG. 16 shows representative microscopic images (40×) of unprocessed control yeast (A), 2nd pass samples exposed to 20 psi back pressure (B), and 40 psi back pressure (C) in Example 3.

Yeast were processed through the O2-HSPH-CM system, with minor modifications to the operating parameters (90 psi (from 100 psi) to the shear unit and 85 psi (from 95 psi) O2) to accommodate differences in slurry viscosity and smooth process flow, then visualized at 40× and quantified for changes in cell density (FIGS. 15-16). Clusters of yeast cells observed in unprocessed control samples appeared to be broken up in processed samples, especially those that were exposed to supersaturating O2. Cell density was reduced in the samples where 20 psi or 40 psi back pressure to the shear unit was applied, −12% and −9% respectively. No cell reduction was observed in samples that were not exposed to supersaturating O2. Higher magnification microscopy revealed that the cell membranes of yeast exposed to excess O2 visually appeared thinner and the intracellular compartment somewhat more opaque. Despite these morphological changes, the cells largely remained intact. After 30 minutes, the yeast slurry was processed through the O2-HSPH-CM a second time. Microscopic inspection and cell counting revealed no significant changes in either morphology or cell density, indicating that a delayed second pass had no significant effects on the process slurry.

Once yeast cells were exposed to supersaturating O2, it was predicted that the cells would swell and cellular membranes would be susceptible to shear forces. In addition, SSO2 causes the generation of ROS and subsequent cell death. The 30 minute delay between process passes was not long enough to cause cell death (typically occurs in 4-6 hours), but may have provided enough time for cells to initiate defense mechanisms that restore cellular integrity, albeit futile in the end. To test this hypothesis, yeast slurry was processed through the O2-HSPH-CM using the same operating parameters as the previous test, then immediately processed a second time through the system. An immediate second process pass caused significant cellular disruption, visualized as widespread debris and quantified by cell counts. The cell density of the slurry was reduced by 36% (20 psi BP) and 34% (40 psi BP) compared to controls that were circulated through the system but not exposed to O2 or shear forces.

Figure 17:
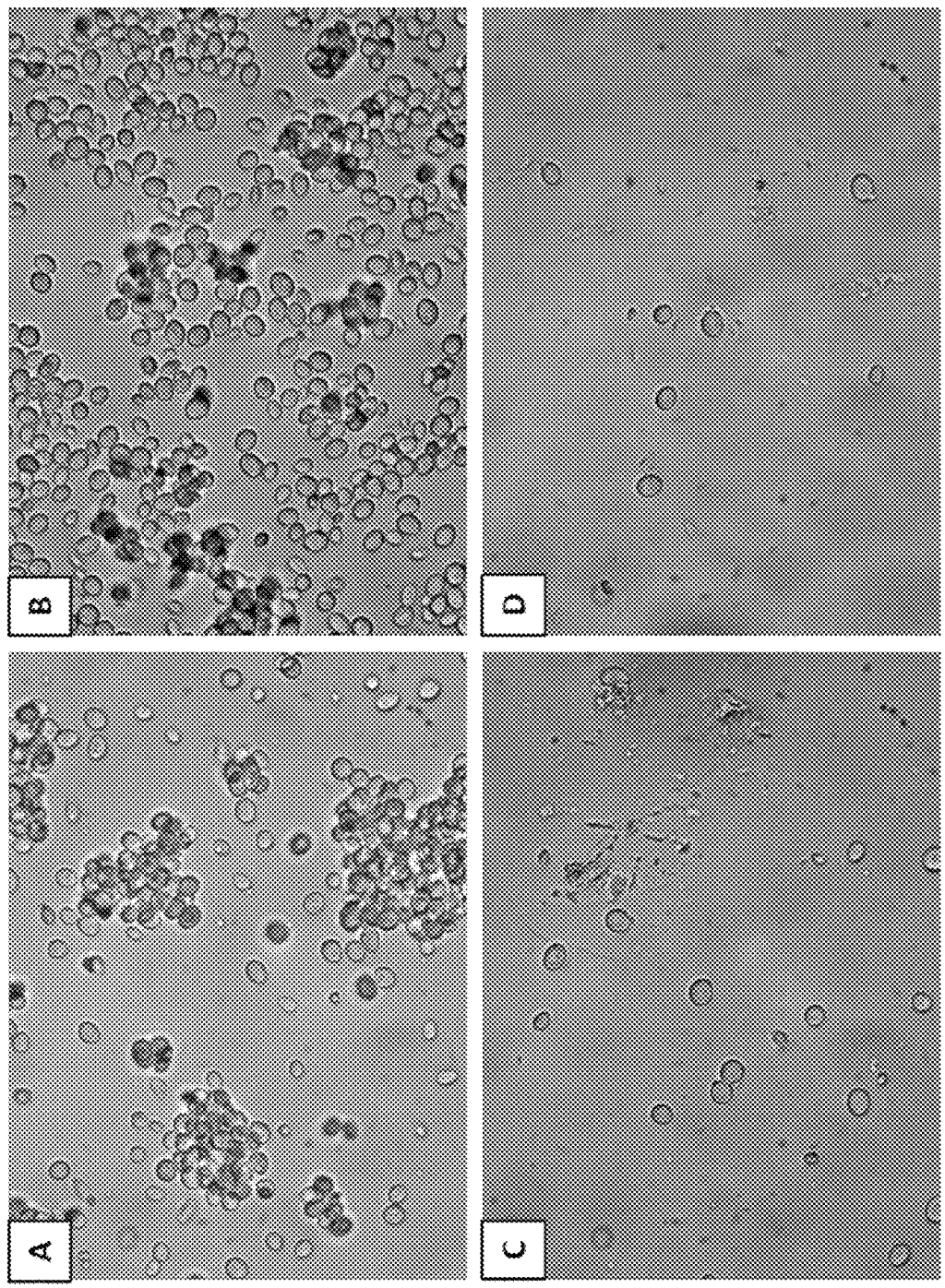
FIG. 17 shows, in Example 3, representative microscopic images (40×) of yeast continuously circulated through the O2-assisted shear (HSPD+CM) system for 5 minutes. (A) unprocessed (circulated, no O2, no high shear processing unit, no colloidal mill) control yeast, (B) high shear processing unit+colloidal mill (no O2), (C) high shear processing unit+colloidal mill, 20 psi back pressure, (D) high shear processing unit+colloidal mill, 40 psi back pressure.

To characterize the effects of multiple passes through the O2-HSPH-CM system, a follow-up test whereby the slurry was continually circulated through the system for 5 minutes was conducted. Each process pass was calculated to require 1.2 minutes. Therefore, an average yeast cell circulating through the system for 5 minutes was exposed to ~4 passes through the system. Widespread debris was again visualized in samples that were exposed to O2-HSPH-CM (FIGS. 17C and 17D), and a further reduction in cell density was likewise documented, −47% (20 psi BP) and −53% (40 psi BP) compared to unprocessed controls (FIG. 17A). Interestingly, O2 appears to be a critical feature for significant yeast disruption through this system. Like the previous tests using shear forces, yeast cells clusters were reduced to single cells, however, the reduction in slurry density was minimal (−15%) (FIG. 17B). Together, these data indicate that shear forces are effective in separating clusters of cells and disrupting O2 saturated cells, and that effective cell lysis occurs immediately following cellular compromise by excess intracellular O2. The system can be further optimized for lysing performance of the O2-high shear processing unit-colloidal mill system and determine the effects on species specific.

Summary.

Despite substantial progress in the development of cell factories for the production of advanced biofuels, there is still need for further improvement in the production capacity of these cell factories and in technologies that extract and recover the synthesized fuel products. Engineered yeast cells are an attractive platform for renewable fuel production, but due to the high tensile strength of yeast membranes, cost-effective lysis of these cells for recovery their fuel products has limited the scalability of this platform. The method as discussed herein whereby O2 is supersaturated into the process stream within a rotational shear device coupled with a colloid mill was shown to rupture >50% of yeast cells within 5 minutes with no added heat or chemical agents. Additional circulation through the system and minor changes to operating procedures will likely increase lysing efficiency further. Unlike simple external shearing forces created by commercial homogenizers, the cellular disruption caused by the O2 O2-high shear processing unit-colloidal mill system is thought to be the result of a different mechanism, namely by creating intracellular disarray, membrane swelling and loss of structural integrity that increases the cell's susceptibility to subsequent shear forces.

Example 4

Demonstration of High Shear Cell Lysing

As shown previously, the gas-assisted high shear process validated that the system is capable of 1) supersaturating algae growth media with CO2 which leads to enhanced CO2 consumption and bioremediation, 2) rupturing a significant fraction of *Chlorella vulgaris* algae or *Saccharomyces* sp. yeast following a single process pass. The process flow path includes a gas-assisted 3-stage high shear unit followed by a colloid mill. Previous cell lysis tests suggested that the first exposure to gas-assisted high shear causes cells within the slurry to take up excess gas and swell, a condition that compromises cell integrity. A second exposure to shear while the cells remain compromised is sufficient to rupture up to 92% of algal cells and 52% of yeast cells. The primary focus of the last set of tests was to identify process flow pressures that optimized cell lysis. Previous tests indicated that a high shear unit rotational speed greater than 15,000 rpm was required to maximize algae cell lysis. Therefore, the rotational speed was increased to 26,000 rpm, a condition that resulted in enhanced algae cell lysis. The rotational speed of the high shear unit was likewise held constant at 26,000 rpm for subsequent yeast lysis testing. For the current tests, we investigated the effect of O2-assisted high shear speed vs. cell lysis.

Materials and Methods. Yeast Biomass Production.

Baker's yeast, *Saccharomyces cerevisiae*, were inoculated into 37° C. dH2O supplemented with 20% D-glucose and 2% bacto yeast extract within 2 L sterilized glass bioreactors supplemented with constant ambient aeration. Culture density was recorded by absorbance at 600 nm. The cultures were scaled up within 20 L glass carboys followed by transfer to 90 L vertical airlift photobioreactors. Cultures near the end of the exponential phase of growth were used for testing.

O2-Assisted High Shear Algae Cell Disruption Set Up and Test Matrix.

Figure 18:
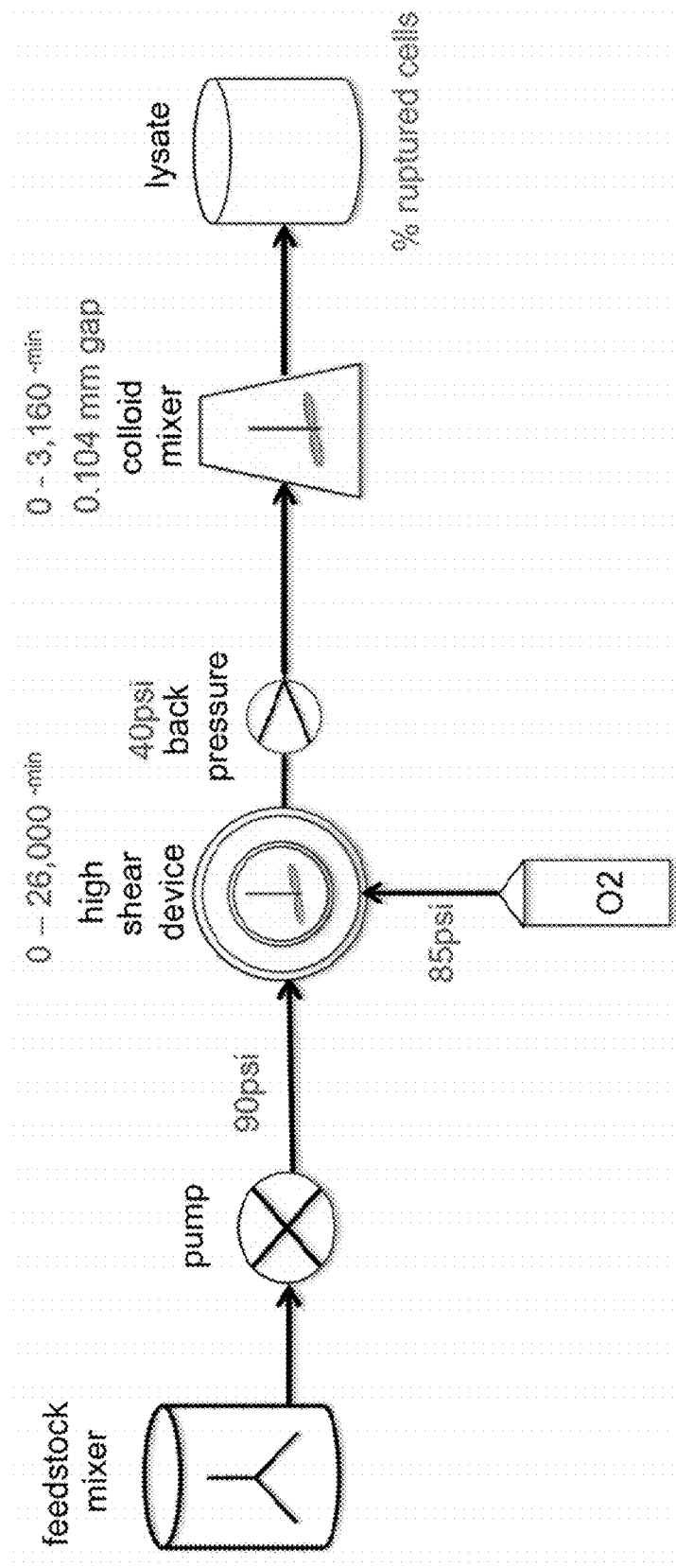
FIG. 18 illustrates a process flow diagram of the cell lysis method and system as discussed in Example 4.

The process flow for O2-assisted high shear yeast cell disruption is shown in FIG. 18. Yeast slurry sample flow was established in rapid succession as follows: the fluid flow pressure of dilute yeast slurry through the system was initiated at 100 psi then adjusted to 90 psi. The high shear unit was then turned on and maintained at a rotational speed of 3,000-26,000 rpm as indicated. Concurrently, diffused O2 was introduced into the system at the shear unit an initial pressure of 100 psi, then adjusted to 85 psi to reduce sample sputtering from the collection nozzle. Control runs were evaluated by running the slurry flowed through the system. The back pressure to the shear unit was adjusted to 40 psi. Once the target test parameters were met, a timer was started. Processed samples were collected 2 minutes later, or after approximately 2 passes through the system, in Erlenmeyer flasks for subsequent cell disruption analyses.

Quantification of Cell Disruption.

The effectiveness of each treatment was qualitatively visualized by bright field microscopy (40×), and quantified by measuring the fraction of physically disrupted cells (Spiden, 2013). ImageJ, a public-domain image processing and analysis software, was used to ensure consistency in cell counting by minimizing variability in analysis between samples. Measurements of the total area occupied by cells were used to verify the intact cell counts. This was particularly useful for samples with cell clumping, typically observed in samples that had been homogenized at higher pressures. All imaging was performed using an AmScope B120C-E1 Siedentopf Binocular Compound Microscope with a 1.3 MP digital camera. Cell counts were compared to unprocessed (flowed through the system but no shear, mill) yeast from the same batch.

Results and Discussion. Effect of Shear Speed on O2-Assisted High Shear Yeast Cell Disruption.

A test matrix in which the operational shear speed of the IKA multi-stage high shear unit was adjusted from 0 rpm (negative control) to 26,000 rpm (see Table 1).

reflecting the optimized speed and gap distance identified in previous tests while the operational speed of the high shear unit was incrementally varied with each process run.

Figure 19:
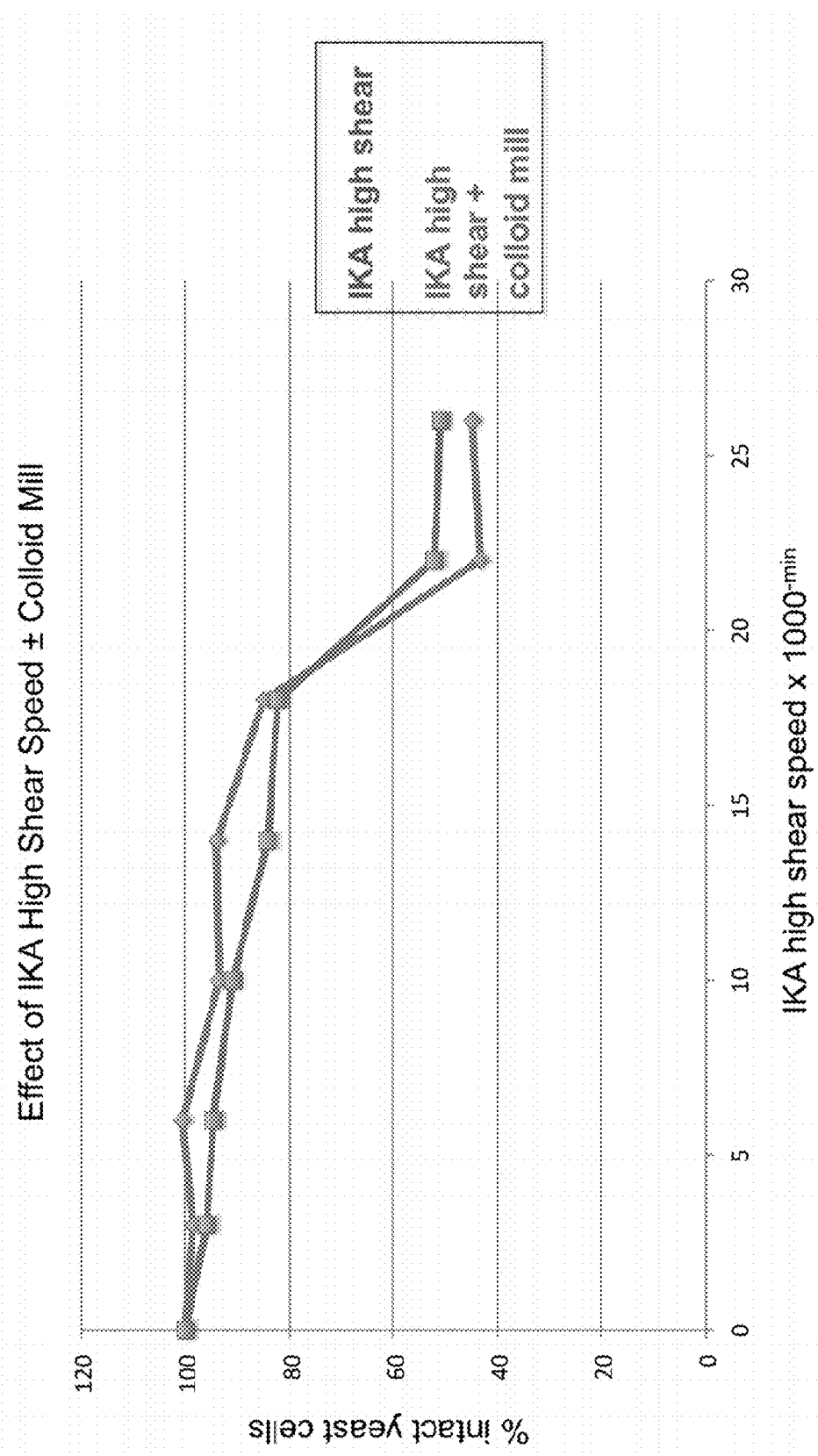
FIG. 19 illustrates the effects of high shear speed on yeast cell lysis assisted by O2 as discussed in Example 4.

FIG. 19 shows a linear relationship between lower shear speeds (3000 rpm-18,000 rpm) and cell disruption. The effect of the downstream colloid mill was minimal. Cell disruption was significantly improved with high shear speeds from 18,000 rpm through 26,000 rpm. Again, the effect of the colloid mill was minimal under this scenario. This result differs from previous testing where the colloid mill increased cell disruption after a single pass. Previous testing showed that after a single pass through the high shear unit at 26,000 rpm, ~70% of yeast cells appeared swollen and stressed, but intact. A subsequent exposure to a shearing mechanism (colloid mill, 3160 rpm, 0.104 mm gap) caused a significant fraction of these compromised cells to lyse. For the current tests, the slurry was circulated for 2 minutes and the slurry was exposed to O2-assisted high shear at least twice, or both the high shear unit plus the colloid mill for 2 minutes for a total of ~4 passes through a shearing mechanism. These data indicate that multiple exposures to O2-assisted high shear at rotational speeds greater than 18,000 rpm is sufficient to rupture ~50-56% of yeast cells within the process stream and that the addition of another downstream shear mechanism may not be necessary.

While preferred embodiments of the invention have been shown and described, modifications thereof can be made by one skilled in the art without departing from the spirit and teachings of the invention. The embodiments described

TABLE 1

Test matrix of O2-assisted high shear speed vs. yeast cell lysis.

| Circulation time (min) 1 pass = 60 s | Pump pressure (psi) | $O_2$ pressure | Back pressure to shear unit (psi) | Shear unit speed | Colloid mill rotor speed (Hz) | Colloid mill clearance gap (mm) | % reduction in cell number (compared to control) |
|---|---|---|---|---|---|---|---|
| Generate sufficient (100 L) yeast culture Start-up procedure | | | | | | | |
| 2 | 90 | 85 | 20 | 26000 | 3160 | 0.104 | 55.2 |
| 2 | 90 | 85 | 20 | 22000 | 3160 | 0.104 | 56.8 |
| 2 | 90 | 85 | 20 | 18000 | 3160 | 0.104 | 15.1 |
| 2 | 90 | 85 | 20 | 14000 | 3160 | 0.104 | 6.2 |
| 2 | 90 | 85 | 20 | 10000 | 3160 | 0.104 | 6.6 |
| 2 | 90 | 85 | 20 | 6000 | 3160 | 0.104 | 0 |
| 2 | 90 | 85 | 20 | 3000 | 3160 | 0.104 | 1.5 |
| 2 | 90 | 85 | 20 | 0 | 3160 | 0.104 | 0 |
| Shut down procedure Start-up procedure | | | | | | | |
| 2 | 90 | 85 | 20 | 26000 | 0 | 0.104 | 49.1 |
| 2 | 90 | 85 | 20 | 22000 | 0 | 0.104 | 47.9 |
| 2 | 90 | 85 | 20 | 18000 | 0 | 0.104 | 17.8 |
| 2 | 90 | 85 | 20 | 14000 | 0 | 0.104 | 16 |
| 2 | 90 | 85 | 20 | 10000 | 0 | 0.104 | 9.2 |
| 2 | 90 | 85 | 20 | 6000 | 0 | 0.104 | 5.4 |
| 2 | 90 | 85 | 20 | 3000 | 0 | 0.104 | 4.3 |
| 2 | 90 | 85 | 20 | 0 | 0 | 0.104 | 0 |
| Shut down procedure Report Total lab time (min) | | | | | | | |

Initially, yeast slurry was circulated through the system while both the high shear unit and colloid mill were not activated. Samples were collected following a 2 minute circulation and the cell density was evaluated and established as 100%. For the first set of shear speed vs. cell disruption tests, the colloid mill operational speed was held at 3160 rpm and the mill gap was held at 0.104 mm, herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of generating products from microorganisms, comprising
   super-saturating a liquid medium with a gas consumable by said microorganisms in a high shear device operating at a shear rate of greater than 1,000,000 $s^{-1}$ to produce a gas-super-saturated (GSS) medium, wherein said GSS medium maintains a GSS level for at least 10 minutes;
   feeding said GSS medium to microorganisms;
   allowing the microorganisms to grow by consuming said gas and generate products via photosynthesis or chemosynthesis; and
   recovering said products.

2. The method of claim 1 wherein said microorganisms are genetically modified.

3. The method of claim 1 wherein said microorganisms include bacteria, protozoa, algae, or fungi, or a combination thereof.

4. The method of claim 1 wherein said gas consumable by said microorganisms is selected from the group consisting of carbon dioxide, nitrogen, air, oxygen, methane, and combinations thereof.

5. The method of claim 1 comprising feeding a nutrient source to the microorganisms in addition to the GSS medium.

6. The method of claim 5 wherein said nutrient source comprises municipal waste; sewage waste; paper pulp; chemical and petrochemical; vegetable including grain, sugar; farm discharge; animal farm discharge including beef, pork, poultry; canning discharge, fishing discharge; farming discharge; food processing discharge.

7. The method of claim 6 wherein said nutrient source is pretreated to eliminate pathogens via gas-assisted high shear lysing of pathogen cells or pretreated using high shear to increase the bio-availability of nutrient in the nutrient source.

8. The method of claim 1 wherein said products include ethane, ethylene, sugars, acids, lipids, ketones, alcohols, amino acids, proteins, or combinations thereof.

9. The method of claim 1 wherein said products are excreted by said microorganisms extracellularly or wherein said products are generated and kept by said microorganisms intracellularly.

10. The method of claim 9 comprising lysing cell of said microorganisms to obtain the products when said products are generated and kept by said microorganisms intracellularly.

11. The method of 10 wherein said lysing comprises
    passing a stream comprising the grown microorganisms through another high shear device; and
    disintegrating cell walls of and intracellular organelles in the microorganisms to release the products.

12. The method of claim 11 wherein said disintegration is enhanced by a penetrating gas capable of permeating the cell wall.

13. The method of claim 12 wherein said enhancement is accomplished by super-saturation of the penetrating gas in the stream or increased gas pressure in a vessel.

14. The method of claim 12 wherein said penetrating gas is different from gas produced by the microorganism cell during respiration.

15. The method of claim 1 further comprising converting at least one of said products to fuel.

* * * * *